United States Patent
Benni et al.

(10) Patent No.: US 9,693,717 B2
(45) Date of Patent: Jul. 4, 2017

(54) METHOD FOR SPECTROPHOTOMETRIC BLOOD OXYGENATION MONITORING OF THE LOWER GASTROINTESTINAL TRACT

(75) Inventors: Paul B. Benni, Acton, MA (US); Robert J. Kopotic, Jamul, CA (US)

(73) Assignee: CAS Medical Systems, Inc., Branford, CT (US)

( * ) Notice: Subject to any disclaimer, the term of this patent is extended or adjusted under 35 U.S.C. 154(b) by 48 days.

(21) Appl. No.: 13/383,391

(22) PCT Filed: Jul. 12, 2010

(86) PCT No.: PCT/US2010/041712
§ 371 (c)(1),
(2), (4) Date: Feb. 14, 2012

(87) PCT Pub. No.: WO2011/006159
PCT Pub. Date: Jan. 13, 2011

(65) Prior Publication Data
US 2012/0136225 A1 May 31, 2012

Related U.S. Application Data

(60) Provisional application No. 61/224,689, filed on Jul. 10, 2009, provisional application No. 61/261,563, (Continued)

(51) Int. Cl.
*A61B 5/1455* (2006.01)
*A61B 5/00* (2006.01)

(52) U.S. Cl.
CPC ........ *A61B 5/14551* (2013.01); *A61B 5/4255* (2013.01); *A61B 5/7271* (2013.01)

(58) Field of Classification Search
CPC . A61B 5/1455; A61B 5/14551; A61B 5/0002; A61B 5/0059; A61B 5/14552
(Continued)

(56) References Cited

U.S. PATENT DOCUMENTS 5,361,759 A * 11/1994 Genevier et al. ............. 600/342
6,456,862 B2    9/2002 Benni et al.
(Continued)

OTHER PUBLICATIONS

Fortune et al. "Cerebro-Splanchnic Oxygenation Ratio (CSOR) Using Near Infrared Specroscopy May be Able to Predict Splanchnic Ischaemia in Neonates", Intensive Care Medicine, vol. 27, No. 8, Jul. 14, 2001, pp. 1401-1407.
(Continued)

*Primary Examiner* — Eric Winakur
*Assistant Examiner* — Chu Chuan (JJ) Liu
(74) *Attorney, Agent, or Firm* — O'Shea Getz P.C.

(57) ABSTRACT

A method and apparatus for non-invasively determining a blood oxygen saturation level and/or the presence of fecal matter within a subject's lower GI tissue is provided. The method includes the steps of: a) providing a spectrophotometric sensor operable to transmit light into the subject's tissue, and to sense the light; b) sensing the subject's lower GI Tissue Using the Sensor, and Producing signal data from sensing the subject's tissue; c) processing the signal data, including determining the presence of one or more wavelength dependent light absorbing materials not present within blood within the subject's lower GI tract from the signal data; and d) determining the blood oxygen saturation level and/or presence of fecal matter within the subject's lower GI tissue, including accounting for the presence of the wavelength dependent light absorbing material not present within blood within the subject's lower GI tract determined using the signal data.

13 Claims, 14 Drawing Sheets

Related U.S. Application Data filed on Nov. 16, 2009, provisional application No. 61/262,419, filed on Nov. 18, 2009, provisional application No. 61/306,200, filed on Feb. 19, 2010.

(58) Field of Classification Search
USPC ....... 600/309, 310, 322, 323, 338, 340, 473, 600/476, 336; 356/41
See application file for complete search history.

(56) References Cited

U.S. PATENT DOCUMENTS

| | | | |
|---|---|---|---|
| 7,047,054 | B2 | 5/2006 | Benni |
| 7,047,055 | B2 * | 5/2006 | Boas et al. .................... 600/338 |
| 7,072,701 | B2 | 7/2006 | Chen et al. |
| 7,113,814 | B2 | 9/2006 | Ward et al. |
| 7,313,427 | B2 | 12/2007 | Benni |
| 7,515,948 | B1 | 4/2009 | Balberg et al. |
| 2004/0034293 | A1 * | 2/2004 | Kimball ......................... 600/323 |
| 2004/0039274 | A1 | 2/2004 | Benaron et al. |
| 2004/0054290 | A1 | 3/2004 | Chance |
| 2008/0097173 | A1 * | 4/2008 | Soyemi .............. A61B 5/14551 600/310 |
| 2009/0182209 | A1 | 7/2009 | Benni |
| 2010/0049018 | A1 | 2/2010 | Duffy et al. |

OTHER PUBLICATIONS

Johnson et al. "The Effect of Meconium on Neonatal and Fetal Reflectance Pulse Oximetry", Journal of Perinatal Medicine 1990, vol. 18, No. 5, 1999, pp. 351-355.

EP search report for EP 10797969.2 dated Mar. 6, 2014.

Friedland et al. "Reflectance Spectrophotometry for the Assessment of Mucosal Perfusion in the Gastrointestinal Tract", Gastrointest Endoscopy Clin N Am, 14 (2004) 539-553.

Communication pursuant to rule 114(2) for EP10797969.2 dated Nov. 3, 2014.

Teller et al. "Continuous Monitoring of Liver Oxygenation with Near Infrared Spectroscopy During Naso-Gastric Tube Feeding in Neonates", Schweizerische Medizinische Wochenschrift 130 (18) 652-56, 2000.

Puyana et al. "Continuous Measurement of Gut pH with Near-Infrared Spectroscopy During Hemorrhagic Shock", Journal of Trauma and Acute Care Surgery 45(1): 201, 1998.

Widder et al. "Use of Near-Infrared Spectroscopy as a Physiologic Monitor for Intra-Abdominal Hypertension", The Journal of Trauma: Injury, Infection , and Critical Care 64 (5): 1165-68, 2008.

Szczapa et al. "Decreased Abdominal Tissue Oxygenation Measured with Near Infrared Spectroscopy in a Premature Extremely Low Birthweight Newborn with Nectrotizing Enterocolitis—Case Report", Early Human Development, 1st International Congree of UENPS, 84, Supplement (November): S106, 2008.

Matcher et al. "Performance Comparison of Several Published Tissue Near-Infrared Spectroscopy Algorithms", Analytical Biochemistry 227 (1): 54-68, 1995.

Fantini et al. "Frequency-Domain Multichannel Optical Detector for Non-Invasive Tissue Spectroscopy and Oximetry", Optical Engineering 34 (1): 32-42, 1995.

Communication pursuant to rule 114(2) for EP10797969.2 dated Apr. 16, 2015.

* cited by examiner

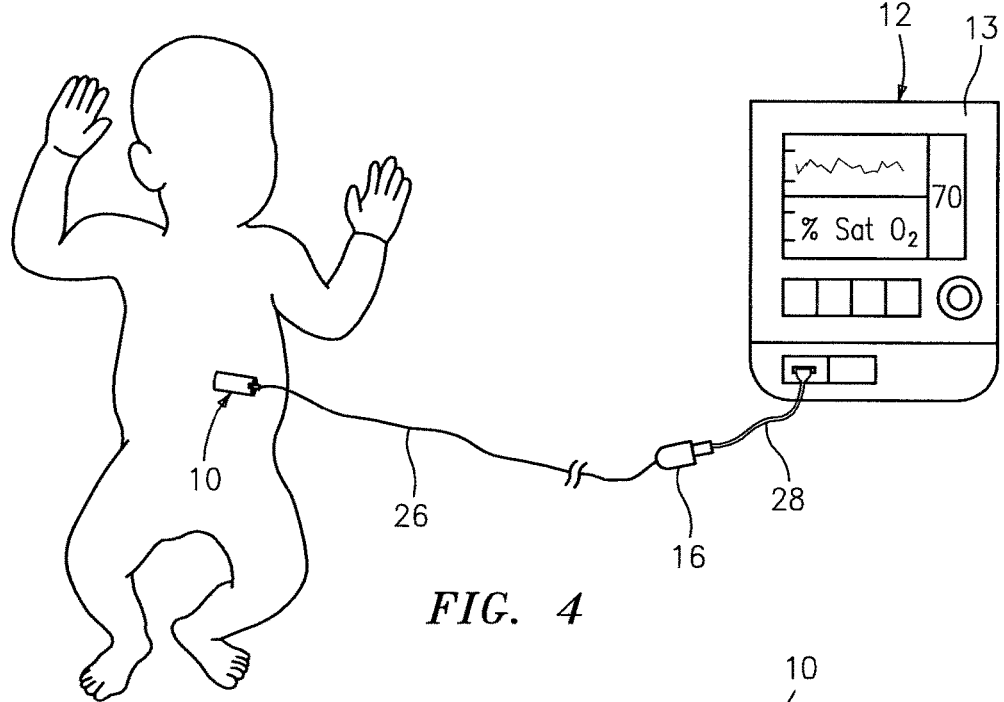
FIG. 4
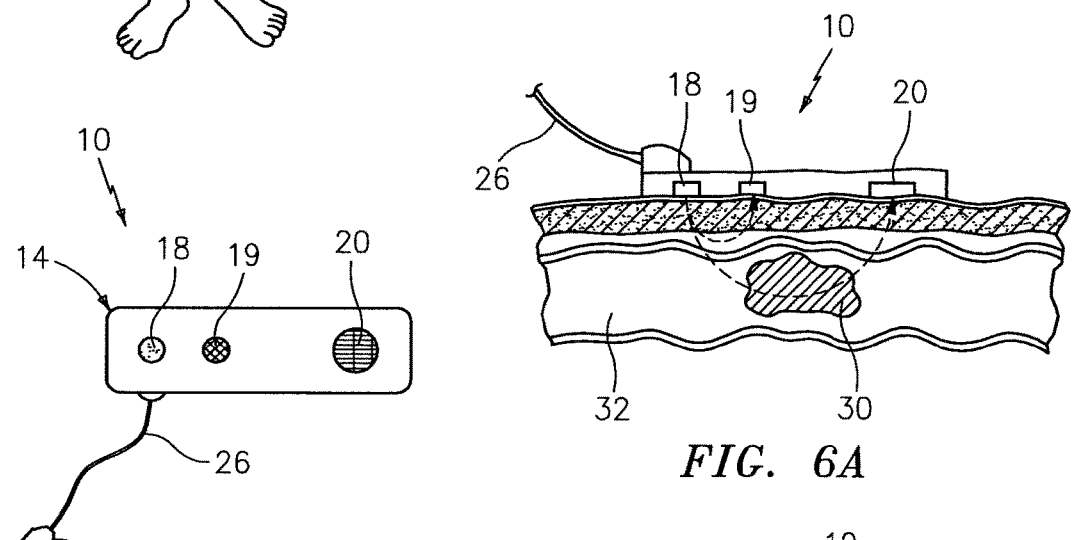
FIG. 5
FIG. 6A
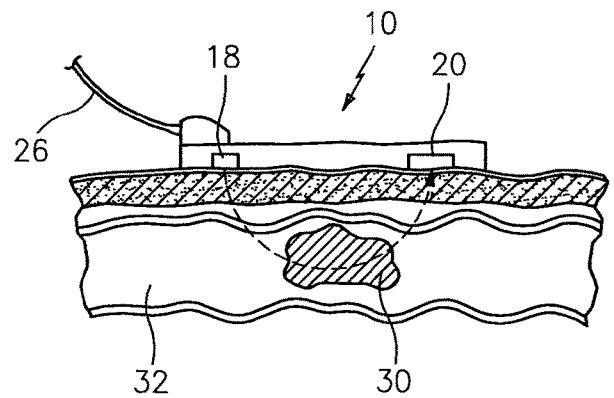
FIG. 6B

| TABLE 1 |||||||
|---|---|---|---|---|---|---|
| Subject # | Study Weight (kg) | Study Age (days) | Study PMA (weeks) | NIRS Interference Level | Percent time of *High* NIRS interference | Outcome |
| *Meconium Stool Subjects* |||||||
| 1 | 0.98 | 8 | 29 | High | 97.0% | NEC +12 days after study |
| 2 | 1.06 | 13 | 29 | Moderate | 1.2% | discharged |
| 3 | 1.35 | 14 | 31 | High | 53.4% | Pneumatosis +35 days after study |
| 4 | 1.30 | 10 | 31 | High | 56.9% | discharged |
| 5 | 1.33 | 7 | 31 | Moderate | 8.7% | discharged |
| *Transitional Stool Subjects* |||||||
| 6 | 1.85 | 9 | 33 | Low | 0.0% | discharged |
| 7 | 1.49 | 21 | 32 | Moderate | 0.0% | discharged |
| 8 | 1.65 | 26 | 32 | Moderate | 0.2% | discharged |
| 9 | 1.61 | 29 | 32 | Moderate | 0.7% | discharged |
| 10 | 1.57 | 38 | 31 | Moderate | 0.0% | discharged |
| 11 | 1.49 | 9 | 35 | Low | 0.1% | discharged |
| 12 | 1.80 | 12 | 34 | High | 15.0% | discharged |
| 13 | 1.53 | 38 | 31 | Low | 0.2% | NEC +1 day after study |
| 14 | 1.24 | 54 | 33 | Moderate | 0.2% | discharged |
| 15 | 1.39 | 21 | 31 | Moderate | 0.1% | discharged |

*FIG. 14*

METHOD FOR SPECTROPHOTOMETRIC BLOOD OXYGENATION MONITORING OF THE LOWER GASTROINTESTINAL TRACT

This application is entitled to the benefit of, and incorporates by reference essential subject matter disclosed in PCT Application No. PCT/US2010/041712 filed on Jul. 12, 2010, which claims priority to U.S. Provisional application Ser. No. 61/224,689 filed on Jul. 10, 2009, U.S. Provisional application Ser. No. 61/261,563 filed on Nov. 16, 2009, U.S. Provisional application Ser. No. 61/262,419 filed on Nov. 18, 2009 and U.S. Provisional application Ser. No. 61/306,200 filed on Feb. 19, 2010.

BACKGROUND OF THE INVENTION

1. Technical Field

This invention relates to methods for non-invasively determining biological tissue oxygenation in general, and to non-invasive methods utilizing near-infrared spectroscopy (NIRS) techniques for determining the same in particular, especially for lower gastrointestinal (GI) oxygenation for a newborn baby.

2. Background Information

U.S. Pat. No. 6,456,862 and U.S. patent application Ser. No. 10/628,068, both assigned to the assignee of the present application and both hereby incorporated by reference, disclose methods for spectrophotometric blood oxygenation monitoring. Oxygen saturation within blood is defined as:

$$O_2 \text{ saturation \%} = \frac{(HbO)_2}{((HbO)_2 + Hb)} * 100\% \quad \text{(Eqn. 1)}$$

These methods, and others known within the prior art, utilize variants of the Beer-Lambert law to account for optical attenuation in tissue at a particular wavelength. Relative concentrations of oxyhemoglobin ($HbO_2$) and deoxyhemoglobin (Hb), and therefore oxygenation levels, within a tissue sample are determinable using changes in optical attenuation:

$$\Delta A_\lambda = -\log\left(\frac{I_{t2}}{I_{t1}}\right)_\lambda = \alpha_\lambda * \Delta C * d * B_\lambda \quad \text{(Eqn. 2)}$$

wherein "$A_\lambda$" represents the optical attenuation in tissue at a particular wavelength λ (units: optical density or OD); "I" represents the incident light intensity (units: $W/cm^2$); "$\alpha_\lambda$" represents the wavelength dependent absorption coefficient of the chromophore (units: $OD*cm^{-1}*\mu M^{-1}$); "C" represents the concentration of chromophore (units: μM); "d" represents the light source to detector (optode) separation distance (units: cm); and "$B_\lambda$" represents the wavelength dependent light scattering differential pathlength factor (unitless). The term "chromophore' as used herein is a material, substance, or molecule that absorbs certain wavelengths of light and reflects others, which results in visible detection of a color (e.g., $HbO_2$ appears reddish in color and Hb appears bluish in color).

To non-invasively determine oxygen saturation within tissue accurately, it is necessary to account for the optical properties (e.g., absorption coefficients or optical densities) of the tissue being interrogated. In some instances, the optical properties for the tissue components that create background light absorption and scattering can be assumed to be relatively constant over a selected wavelength range. In other instances, they cannot accurately be assumed to be constant. FIG. 1 illustrates an example of the relationship between the optical properties of tissue and the scattering losses and the background tissue absorption losses.

In some instances, the region of the subject being interrogated may contain chromophores other than Hb and HbO2, which unless accounted for, can adversely affect the determination of Hb and HbO2. When NIRS techniques are used to monitor lower GI oxygenation in neonates, for example, chromophores to be accounted for include components of neonatal meconium stools, transitional stools, and certain nutritional fluids, all of which have a wavelength dependent absorption spectra in the same wavelength range as Hb and HbO2, as shown in FIG. 1. A NIRS algorithm that does not compensate for neonatal stools, particularly meconium, will very likely give an inaccurate measurement of lower GI tissue oxygenation. Specifically, the inaccurate measurement will often erroneously indicate a decreased lower GI oxygenation level, because the absorption spectra of meconium and certain nutritional fluids mimics deoxygenated hemoglobin (Hb).

Meconium stools are typically passed by a neonate during its first two or three days of life. Meconium stools are quickly followed by transitional stools by in the 4 to 5 days of age range. Meconium is a composite of desquamated intestinal lining, mucous, blood and bile. Bilirubin and biliverdin found within liver bile can influence the color of a stool when present within the stool. Bilirubin is formed by the liver from hemoglobin that is released during the end of life-cycle for red blood cells. Referring to FIG. 2, as hemoglobin is broken down, heme is converted to biliverdin by heme oxygenase. Then biliverdin is converted to bilirubin by biliverdin reductase. Depending on the concentration of bilirubin and biliverdin, bile can vary from almost black to green and light yellow in color. A fresh specimen of day-old meconium has been determined to typically have a peak transmittance (i.e. low light absorption) of about 900 nm. While the composition of meconium is unique in its high concentration of bile and other aspects, follow-on stools such as transitional stools may also have chromophores in or near the absorbance range associated with Hb and HbO2. In particular high concentrations of biliverdin in transitional stools, which makes the stool appear green in color, has a distinctive absorbance spectra, similar to that of meconium as shown in FIG. 3. The absorbance spectra of isolated biliverdin as shown in FIG. 3A demonstrates this characteristic, while the absorption spectra of isolated bilirubin (see FIG. 3B) does not. Because bile is present in the liver and gall bladder which can contain biliverdin, high concentrations of bile can adversely affect the determination of Hb and HbO2 by NIRS monitoring of these organs as well.

Iron containing fluids commonly used to meet the enterally delivered nutritional needs of infants (e.g., breast milk and infant formula) are examples of nutritional fluids. While the exact chemical makeup of breast milk is still unknown, the composition of infant formula is formulated to be similar to the generally accepted makeup. An example of the mismatch between breast milk and formula that is pertinent to the present application is the amount and uptake of iron; e.g., breast milk contains about 0.3 mg of iron per liter, of which nearly half is absorbed, and formula contains about 10 mg of iron per liter, of which less than 5% is absorbed. Iron salts are the common source for fortifying infant formula (ferrous fumarate, ferrous sulfate, and ferrous gluconate). Other chromophores are likely present in these two fluids. In addition to iron, the U.S. Food and Drug Administration (FDA) specifies that infant formula must contain: fat, protein, niacin, folic acid, linoleic acid, pantothenic acid, calcium, chloride, copper, iodine, manganese, magnesium, phosphorous, potassium, sodium, and zinc, and vitamins A, B, B1, B2, B12, C, D, E, and K. In addition, formulas not made with cow's milk must include biotin, choline and inositol. A formula frequently given to neonates during a neonate intensive care unit stay is Enfamil® brand infant formula (iron fortified, premature lipil) marketed by Mead Johnson & Company. The Enfamil® formula was found to have a peak transmittance of about 850 nm. The term "transmittance", as used herein, refers to the amount of light that passes through the material; i.e., the inverse of absorbance.

The timing and volume of enteral nutrition by caregivers is rather subjective, especially for infants at risk for bowel-related diseases, e.g., necrotizing enterocolitis (NEC) and perforation of the gastrointestinal tract. While the etiology of these diseases is mixed and not fully understood, it is believed that ischemia plays a common critical role. Until enteral feeds are tolerated, parenteral or intravenous sources of nutrition are administered (a more invasive and largely less effective methodology).

What is needed, therefore, is a method for non-invasively determining the level of oxygen saturation and related ischemia within lower GI tissue, which method is operable to account for materials potentially within the lower GI tract that have a wavelength dependent absorption spectra (e.g., meconium, including stool components such as biliverdin, and/or nutritional fluids, etc.) that would, if unaccounted for, affect the accuracy of the oxygen saturation determination.

What is also needed, therefore, is a method for non-invasively determining the level of oxygen saturation and related ischemia within the viscera (GI, liver, kidneys, pancreas, stomach), which method is operable to account for materials potentially within the viscera that have a wavelength dependent absorption spectra (certain nutritional fluids) that would, if unaccounted for, affect the accuracy of the oxygen saturation determination.

DISCLOSURE OF THE INVENTION

Premature infants must adapt to extra-uterine life during a period in which many organ systems are not yet fully matured. Among these organ systems is the gastrointestinal (GI) system, whose immaturity predisposes the infant to several co-morbidities including feeding intolerance, susceptibility to bacterial invasion and infection, the development of necrotizing enterocolitis (NEC), and gastric perforation. While several studies have validated the use of a NIRS monitor to measure cerebral saturations, little data is available within the prior art regarding oxygenation of mesenteric tissue. It is believed that such data may be quite useful, particularly in the setting of a preterm infant who is at higher risk for the aforementioned co-morbidities. According to the present invention, a NIRS device may be used to evaluate and provide baseline saturations for mesenteric tissue.

According to an aspect of the present invention, a method for non-invasively determining a blood oxygen saturation level within a subject's lower GI tissue is provided. The method includes the steps of: a) providing a spectrophotometric sensor operable to transmit light into the subject's tissue, and to sense the light; b) sensing the subject's lower GI tissue using the sensor, and producing signal data from sensing the subject's tissue; c) processing the signal data, including determining the presence of one or more wavelength dependent light absorbing materials not present within blood within the subject's lower GI tract from the signal data; and d) determining the blood oxygen saturation level within the subject's lower GI tissue, including accounting for the presence of the wavelength dependent light absorbing material not present within blood within the subject's lower GI tract determined using the signal data.

According to another aspect of the present invention, a method for non-invasively determining the presence of fecal matter within the lower GI tract of a subject is provided. The method includes the steps of: a) providing a spectrophotometric sensor operable to transmit light at a plurality of wavelengths into the subject's tissue, and to sense the light; b) sensing the subject's lower GI tissue using the sensor, and producing signal data from sensing the subject's tissue; and c) processing the signal data, including determining the presence of fecal matter within the subject's lower GI tract based on the presence of at least one of meconium, including stool components such as biliverdin, and/or nutritional fluids within the subject's lower GI tract, wherein the presence of meconium, including stool components such as biliverdin, and/or nutritional fluid is determined using a difference in attenuation between the wavelengths.

According to another aspect of the present invention, a near-infrared spectroscopy apparatus is provided. The apparatus includes a spectrophotometric sensor and a processor. The sensor has at least one light source and at least one light detector. The sensor is operable to transmit light into a subject's tissue, to sense the transmitted light, and to produce signal data from the sensed light. The processor is adapted to receive and process the signal data to determine the presence of a wavelength dependent light absorbing material not present within blood within the subject's lower GI tract.

According to another aspect of the present invention, an apparatus for non-invasively determining the presence of fecal matter within a lower GI tract of a subject is provided. The apparatus includes at least one spectrophotometric sensor and a processor. The sensor has at least one light source and at least one light detector. The sensor is operable to transmit light at a plurality of wavelengths into the subject's tissue, and to sense the light. The processor is adapted to receive the signal data and to process the signal data to determine the presence of fecal matter within the lower GI tract of the subject. The processing includes determining the presence of a wavelength dependent light absorbing material found within fecal matter.

The present method and apparatus provides advantageous accuracy. All prior art non-invasive devices and methods for determining blood oxygen saturation level within a subject's lower GI tissue, of which we are aware, do not consider the optical characteristics of materials (e.g., meconium, including stool components such as biliverdin, and/or nutritional fluids) commonly found within the lower GI tract of the subject that have a wavelength dependent absorption spectra If the optical characteristics of these materials (e.g., meconium, including stool components such as biliverdin, and/or nutritional fluids) are not considered in the algorithm to measure lower GI tissue oxygen saturation, the determined oxygen saturation value will likely be inaccurate.

NIRS sensors are typically calibrated by use of assumed constants and/or relative to a source (e.g., a phantom sample, empirical data, etc.) other than subject being sensed; i.e., calibrated in a "subject independent" manner. The present device and method, in contrast, considers the specific physical characteristics of other wavelength dependent light absorbing compounds in a particular subject's lower GI tract such as meconium and/or ingested nutritional fluids, by sensing the particular subject's lower GI tissue, creating signal data based on the sensing, and determining accurate lower GI tissue oxygenation in the presence of these materials (e.g., meconium, including stool components such as biliverdin, and/or nutritional fluids).

These and other objects, features, and advantages of the present invention method and apparatus will become apparent in light of the detailed description of the invention provided below and the accompanying drawings. The methodology and apparatus described below constitute a preferred embodiment of the underlying invention and do not, therefore, constitute all aspects of the invention that will or may become apparent by one of skill in the art after consideration of the invention disclosed overall herein.

BRIEF DESCRIPTION OF THE DRAWINGS

FIG. 4 is a diagrammatic representation of a NIRS sensor placed on a subject's lower abdomen area to interrogate the bowel and its contents: meconium and nutritional fluid.

FIG. 5 is a diagrammatic view of a NIRS sensor.

FIG. 6A is a diagrammatic representation of a NIRS sensor embodiment showing light interrogating bowel and its contents: meconium and nutritional fluid.

FIG. 6B is a diagrammatic representation of a NIRS sensor embodiment showing light interrogating bowel and its contents: meconium and nutritional fluid.

FIG. 14 is a table containing study data.

DETAILED DESCRIPTION THE INVENTION

Figure 1:
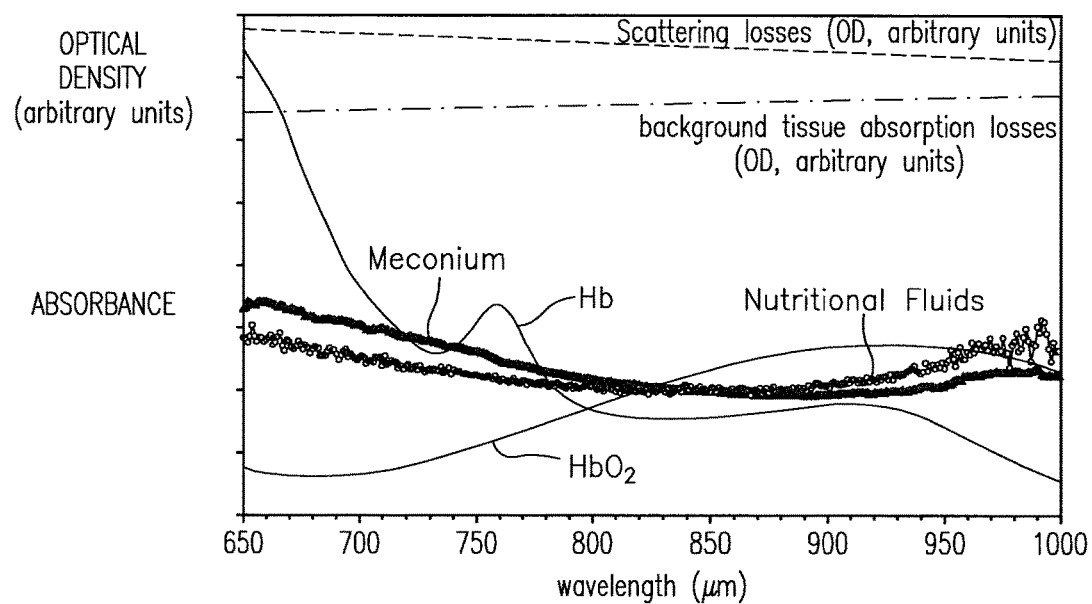
FIG. 1 is a graph diagrammatically illustrating tissue data plotted relative to a Y-axis of values representative of light absorbance, and an X-axis of wavelength values.

Referring to FIG. 4, a near-infrared spectrophotometric (NIRS) system 8 is provided that includes at least one sensor 10 and a processor portion 12. The sensor 10 is capable of transmitting a light signal into the tissue of a subject and sensing the light signal once it has passed through the lower GI tissue and materials contained within the lower GI tract via transmittance or reflectance. The present method and apparatus can be used with a variety of NIRS sensors, and is not therefore limited to any particular NIRS sensor.

Referring to FIGS. 1, 5, 6A, and 6B, an example of an acceptable NIRS sensor 10 includes an assembly housing 14 and a connector housing 16. The assembly housing 14 is a flexible structure that can be attached directly to a subject's body. The sensor 10 includes one or more light sources 18 and light detectors 19, 20. The sensor embodiment shown in FIGS. 5 and 6A has a pair of light detectors 19, 20. The sensor embodiment shown in FIG. 6B has a single light detector 20. A disposable adhesive envelope or pad is preferably used for mounting the assembly housing 14 easily and securely to the subject's skin. Light signals of known but different wavelengths from the light sources 18 emit through a prism assembly. The light sources 18 are preferably laser diodes that emit light at a narrow spectral bandwidth at predetermined wavelengths. The laser diodes may be mounted remote from the assembly housing 14; e.g., in the connector housing 16 or within the processor portion 12. In these embodiments, a fiber optic light guide is optically interfaced with the laser diodes and the prism assembly that is disposed within the assembly housing 14. In other embodiments, the light sources 18 are mounted within the assembly housing 14. A first connector cable 26 connects the assembly housing 14 to the connector housing 16 and a second connector cable 28 connects the connector housing 16 to the processor portion 12. The light detectors 19, 20 each include one or more photodiodes. The photodiodes are also operably connected to the processor portion 12 via the first and second connector cables 26, 28. Other examples of acceptable NIRS sensors are described in U.S. patent application Ser. Nos. 12/090,671 and 12/514,671, and U.S. Pat. Nos. 7,047,054 and 7,313,427, all of which are commonly assigned to the assignee of the present application and all of which are hereby incorporated by reference in their entirety.

The processor portion 12 includes a processor 13 having a central processing unit (CPU) adapted (e.g., programmed) to selectively perform the functions necessary to perform the present analysis as described herein. For example, the processor 13 is adapted to operate the sensor 10 to emit light signals from the light source 18, and to receive sensor signals from the light detectors 19, 20. The processor is further adapted to process the sensor signals according to the method and algorithm described herein. It should be noted that the functionality of processor 13 may be implemented using hardware, software, firmware, or a combination thereof. A person skilled in the art would be able to program the processor to perform the functionality described herein without undue experimentation.

The exemplary algorithm embodiment described herein characterizes a change in attenuation as a function of the difference in attenuation between different wavelengths. The algorithm accounts for the effects of pathlength and parameter "E", which represents energy losses ("G") due to light scattering within tissue, other background absorption losses ("F") from biological compounds, and other unknown losses ("N") including measuring apparatus variability (E=G+F+N). As will be discussed below, the parameter "E" reflects energy losses not specific to the subject being tested with a calibrated sensor (i.e., "subject-independent").

The absorption $A_{b\lambda}$ detected from the deep light detector 20 includes attenuation and energy losses from both the deep and shallow tissue, while the absorption $A_{x\lambda}$ detected from the shallow light detector 19 includes attenuation and energy losses from shallow tissue. Absorptions $A_{b\lambda}$ and $A_{x\lambda}$ can be expressed in the form of Equation 3 and Equation 4:

$$A_{b\lambda} = -\log\left(\frac{I_b}{I_o}\right)_\lambda = \alpha_\lambda * C_b * L_b + \alpha_\lambda * C_x * L_x + E_\lambda \quad \text{(Eqn. 3)}$$

$$A_{x\lambda} = -\log\left(\frac{I_x}{I_o}\right)_\lambda = \alpha_\lambda * C_x * L_x + E_{x\lambda} \quad \text{(Eqn. 4)}$$

In some applications, a single light detector may be used (e.g., see FIG. 6B), in which case Equation 5 can be used:

$$A_{b\lambda} = -\log(I_b/I_o)_\lambda = \alpha_\lambda * C_b * L_b + E_\lambda \quad \text{(Eqn 5)}$$

If both the deep and shallow detectors are used, then substituting Equation 4 into Equation 3 yields $A'_\lambda$, which represents attenuation and energy loss from deep tissue only:

$$A'_\lambda = A_{b\lambda} - A_{x\lambda} = \alpha_\lambda * C_b * L_b + (E_\lambda - E_{x\lambda}) \quad \text{(Eqn.6)}$$

From Equation 5 or Equation 6, L is the effective pathlength of the photon traveling through the deep tissue and $A'_1$ and $A'_2$ represent light attenuation at two different wavelengths to determine differential wavelength light attenuation $\Delta A'_{12}$:

$$A'_1 - A'_2 = \Delta A'_{12} \quad \text{(Eqn.7)}$$

Substituting Equation 5 or 6 into Equation 7 for $A'_1$ and $A'_2$, $\Delta A'_{12}$ can be expressed as:

$$\Delta A'_{12} = \alpha_{\lambda 12} * C_b * L_b + \Delta E_{12} \quad \text{(Eqn.8)}$$

and Equation 8 can be rewritten in expanded form:

$$\Delta A'_{12} = \langle (\alpha_{r1} - \alpha_{r2})[Hb]_b + (\alpha_{o1} - \alpha_{o2})[HbO_2]_b \rangle * L_b + (E'_1 - E'_2) = (\Delta \alpha_{r12} * [Hb]_b * L_b) + (\Delta \alpha_{o12} * [HbO_2]_b * L_b) + \Delta E'_{12} \quad \text{(Eqn.9)}$$

where:
$(\Delta \alpha_{r12} * [Hb]_b * L_b)$ represents the attenuation attributable to Hb; and
$(\Delta \alpha_{o12} * [HbO_2]_b * L_b)$ represents the attenuation attributable to $HbO_2$; and
$\Delta E'_{12}$ represents energy losses due to light scattering within tissue, other background absorption losses from biological compounds, and other unknown losses including measuring apparatus variability.

The multivariate form of Equation 9 is used to determine $[HbO_2]_b$ and $[Hb]_b$ with three different wavelengths:

$$\begin{bmatrix} \Delta A'_{12} & \Delta E'_{12} \\ \Delta A'_{13} & \Delta E'_{13} \end{bmatrix} (L_b)^{-1} = \begin{bmatrix} \Delta \alpha_{r12} & \Delta \alpha_{o12} \\ \Delta \alpha_{r13} & \Delta \alpha_{o13} \end{bmatrix} \begin{bmatrix} [Hb]_b \\ [HbO_2]_b \end{bmatrix} \quad \text{(Eqn. 10)}$$

Rearranging and solving for $[HbO_2]_b$ and $[Hb]_b$, simplifying the $\Delta \alpha$ matrix into $[\Delta \alpha']$:

$$\begin{bmatrix} \Delta A'_{12} \\ \Delta A'_{13} \end{bmatrix} [\Delta \alpha']^{-1} (L_b)^{-1} - \begin{bmatrix} \Delta E'_{12} \\ \Delta E'_{13} \end{bmatrix} [\Delta \alpha']^{-1} (L_b)^{-1} = \begin{bmatrix} [Hb]_b \\ [HbO_2]_b \end{bmatrix} \quad \text{(Eqn. 11)}$$

Then combined matrices $[\Delta A'] [\Delta \alpha']^{-1} = [A_c]$ and $[\Delta E][\Delta \alpha']^{-1} = [\Psi_c]$:

$$\begin{bmatrix} A_{Hb} \\ A_{HbO_2} \end{bmatrix} (L_b)^{-1} - \begin{bmatrix} \Psi_{Hb} \\ \Psi_{HbO_2} \end{bmatrix} (L_b)^{-1} = \begin{bmatrix} [Hb]_b \\ [HbO_2]_b \end{bmatrix} \quad \text{(Eqn. 12)}$$

The parameters $A_{Hb}$ and $A_{HbO2}$ represent the product of the matrices $[\Delta A_\lambda]$ and $[\Delta \alpha']^{-1}$ and the parameters $\Psi_{Hb}$ and $\Psi_{HbO2}$ (referred to hereinafter as calibration constants) represent the product of the matrices $[\Delta E'_\lambda]$ and $[\Delta \alpha']^{-1}$. To determine the level of tissue blood oxygen saturation ($SnO_2$), Equation 12 is rearranged using the form of Equation 1 and is expressed as follows:

$$SnO_2 \% = \frac{(A_{HbO_2} - \Psi_{HbO_2})}{(A_{HbO_2} - \Psi_{HbO_2} + A_{Hb} - \Psi_{Hb})} * 100\% \quad \text{(Eqn. 13)}$$

Note that tissue blood oxygen saturation is sometimes symbolized as $StO_2$, $SctO2$, $CrSO_2$, or $rSO_2$. The effective pathlength $L_b$ cancels out in the manipulation from Equation 12 to Equation 13.

The value for $SnO_2$ is initially determined from an empirical reference of weighted combination of venous and arterial oxygen saturation ($SmvO_2$) value, for example using:

$$SmvO_2 = Kv * SvO_2 + Ka * SaO_2 \quad \text{(Eqn.14)}$$

and the empirically determined values for $SvO_2$ and $SaO_2$, where the term "$SvO_2$" represents venous oxygen saturation, the term "$SaO_2$" represents arterial oxygen saturation, and the terms Kv and Ka are the weighted venous and arterial contributions respectively (Kv+Ka=1). The empirically determined values for $SvO_2$ and $SaO_2$ are based on data developed by discrete sampling (e.g., samples collected at points in time spaced apart from one another) or continuous monitoring of the subject's blood performed at or about the same time as the sensing of the tissue with the sensor; e.g., blood samples discretely collected can be analyzed by blood gas analysis and blood samples continuously monitored can be analyzed using a fiber optic catheter inserted within a blood vessel. The temporal and physical proximity of the NIRS sensing and the development of the empirical data helps assure accuracy. The initial values for Kv and Ka within Equation 14 are clinically reasonable values for the circumstances at hand. The values for $A_{HbO2}$ and $A_{Hb}$ are determined mathematically using the values for $I_{b\lambda}$ and $I_{x\lambda}$ for each wavelength sensed with the NIRS sensor (e.g., using Equation 3 & 4 for deep and shallow detectors or Equation 5 for a single detector). The calibration parameters $\Psi_{Hb}$ and $\Psi_{HbO2}$, which account for energy losses due to scattering as well as other background absorption from biological compounds, are then determined using Equation 14 and non-linear regression techniques by correlation to different weighted values of $SvO_2$ and $SaO_2$; i.e., different values of Ka and Kv. Statistically acceptable values of Kv and Ka and $\Psi_{Hb}$ and $\Psi_{HbO2}$ are converged upon using the non-linear regression techniques. Experimental findings show that with proper selection of Ka and Kv, the calibration parameters $\Psi_{Hb}$ and $\Psi_{HbO2}$ are constant within a statistically acceptable margin of error for an individual NIRS sensor used to monitor brain oxygenation on different human subjects.

The above-identified process produces a NIRS system 8 calibrated relative to a particular subject using invasive techniques (i.e., subject specific calibration), or a NIRS system 8 calibrated relative to an already calibrated sensor 10 (or relative to a phantom sample); i.e., subject independent calibration. The present device and method provides the advancement of also considering the specific physical characteristics of other wavelength dependent light absorbing compounds 30 (see FIG. 6) in the lower GI tract 32 such as meconium and/or nutritional fluids, of the particular subject by sensing the subject's lower GI tissue.

Figure 7:
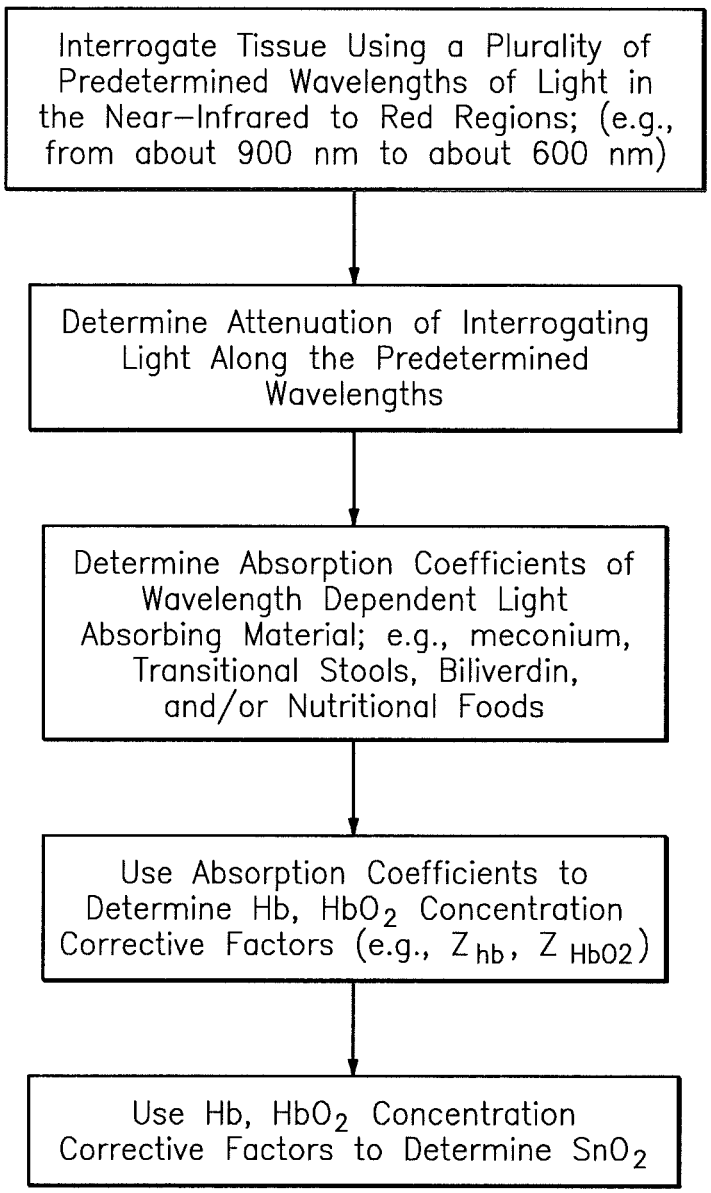
FIG. 7 is a flow chart illustrating steps according to one aspect of the present invention.

To compensate for wavelength dependent light absorbing materials such as meconium and/or nutritional fluids in the GI tract of a newborn baby, the effects of the aforesaid chromophores can be accounted for within one or more algorithms programmed into the processor. The flow chart shown in FIG. 7 illustrates an embodiment of the present algorithm. FIG. 1 shows the absorbance of meconium and/or nutritional fluids from a laboratory spectrometer measurement plotted with the familiar absorbance of Hb and $HbO_2$. The term "absorbance" as used in the Y-axis of FIG. 1 and other Figures herein refers to a arbitrary measure of the relationship of the light incident to the tissue and the light sensed from the tissue; e.g., the amount of light absorbed, the extinction coefficient, etc. One way to compensate for meconium and or nutritional fluids as they pass through the bowels of the baby is to use the sensed signal data to create a meconium and food (MECf) index value. The MECf index value is derived from wavelength dependent light attenuation attributable to the optical characteristics of meconium, including stool components such as biliverdin, and nutritional fluids (e.g., as shown in FIG. 1). Index values for other wavelength dependent light absorbing materials can also be determined using the process described herein. Note that the presence of meconium has a much greater effect in NIRS light measurement compared to melanin (the light absorbing pigmentation in skin and tissue) in babies. This is partially due to reduced skin pigmentation in the newborn, especially for newborns and in particular for very low birth weight (VLBW) babies, in which the skin has not fully developed and where the incidence of bowel disease is high. To determine the absorption coefficient of meconium and/or nutritional fluids ($\alpha_{MECf}$) for the particular wavelengths of light used in the interrogation of the tissue, a lookup table can be employed based on the data depicted graphically in FIG. 1, or a non-linear regression modeled equation such as that shown below where the variables A, B, K, and Z are assigned values are based on a non-linear regression fit of a particular set of data:

$$\alpha_{MECf} = Z + A^* \exp(K^* \text{wavelength}/1000) + B^* \exp(M^* \text{wavelength}/1000) [\text{cm}^{-1}]$$

To determine the MECf index value, one or more of the wavelengths in the near-infrared region to the red region (i.e., from about 900 nm to about 600 nm; e.g., 690 nm, 780 nm, 805 nm, 850 nm) are sensed, using sensors applied to the subject. When sensing for meconium and/or nutritional fluids, red wavelengths are favored because red light is more sensitive to the presence of meconium and/or nutritional fluids than infrared light. Lower wavelengths of light could also be used, but suffer from relative increased attenuation from the higher tissue and hemoglobin absorption coefficients, resulting in reduced tissue penetration, reduced detected light signal strength, and resultant poor signal to noise ratio.

To calculate the MECf index value (identified in Equation 15 as "MECf"), a four wavelength, three unknown differential attenuation algorithm (following similarly to the derivation shown by Equations 3-10), is used such as that shown in Equation 15:

$$\begin{bmatrix} \Delta A_{\lambda 12} \\ \Delta A_{\lambda 13} \\ \Delta A_{\lambda 14} \end{bmatrix} (L_b)^{-1} = \begin{bmatrix} \Delta \alpha'_{r12} & \Delta \alpha'_{o12} & \Delta \alpha'_{MECf12} \\ \Delta \alpha'_{r13} & \Delta \alpha'_{o13} & \Delta \alpha'_{MECf13} \\ \Delta \alpha'_{r14} & \Delta \alpha'_{o14} & \Delta \alpha'_{MECf14} \end{bmatrix} \begin{bmatrix} Hb \\ HbO2 \\ MECf \end{bmatrix} \quad \text{(Eqn. 15)}$$

Alternatively, Equation 16 shown below could be used. Equation 16 accounts for energy losses "E" as described above:

$$\begin{bmatrix} \Delta A_{\lambda 12} & \Delta E'_{\lambda 12} \\ \Delta A_{\lambda 13} & \Delta E'_{\lambda 13} \\ \Delta A_{\lambda 14} & \Delta E'_{\lambda 14} \end{bmatrix} \quad \text{(Eqn. 16)}$$

$$(L_b)^{-1} = \begin{bmatrix} \Delta \alpha'_{r12} & \Delta \alpha'_{o12} & \Delta \alpha'_{MECf12} \\ \Delta \alpha'_{r13} & \Delta \alpha'_{o13} & \Delta \alpha'_{MECf13} \\ \Delta \alpha'_{r14} & \Delta \alpha'_{o14} & \Delta \alpha'_{MECf14} \end{bmatrix} \begin{bmatrix} Hb \\ HbO2 \\ MECf \end{bmatrix}$$

The MECf index value determinable from Equations 15 or 16 accounts for the presence of meconium and/or nutritional fluids in the bowels of a subject being interrogated by a NIRS sensor and can be converted to a "corrective" factor used to determine accurate tissue blood oxygen saturation $SnO_2$ within the GI tract of that subject. In some embodiments, the MECf index value can be used with a database to determine subject-specific corrective factors (e.g., $Z_{Hb}$ and $Z_{HbO2}$) for the calculation of Hb and HbO2 concentrations. The database contains data, at least some of which are empirically collected, pertaining to different oxyhemoglobin (HbO2), deoxyhemoglobin (Hb), and meconium (and/or nutritional fluid) concentrations. The concentration data are organized relative to a range of MECf index values in a manner that enables the determination of Hb and HbO2 concentration corrective factors (e.g., $Z_{Hb}$ and $Z_{HbO2}$). The organization of the information within the database can be accomplished in a variety of different ways.

Figure 8:
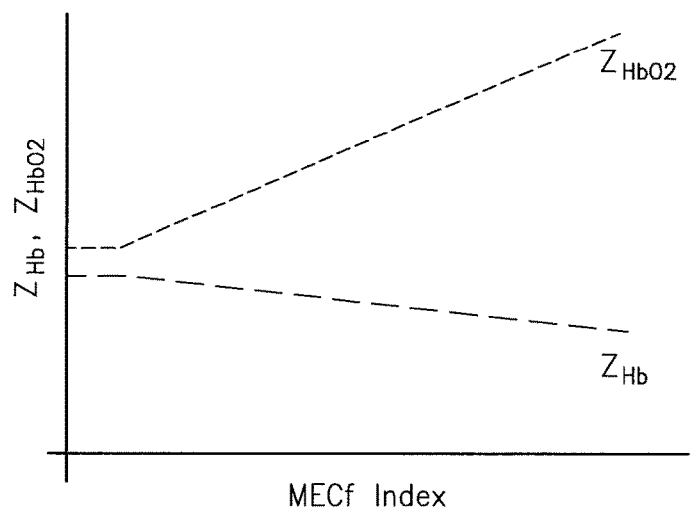
FIG. 8 is a graph having values diagrammatically representative of subject-specific calibration coefficients (ZHb, ZHbO2) plotted along a Y-axis, MECf index values plotted along an X-axis.
Figure 2:
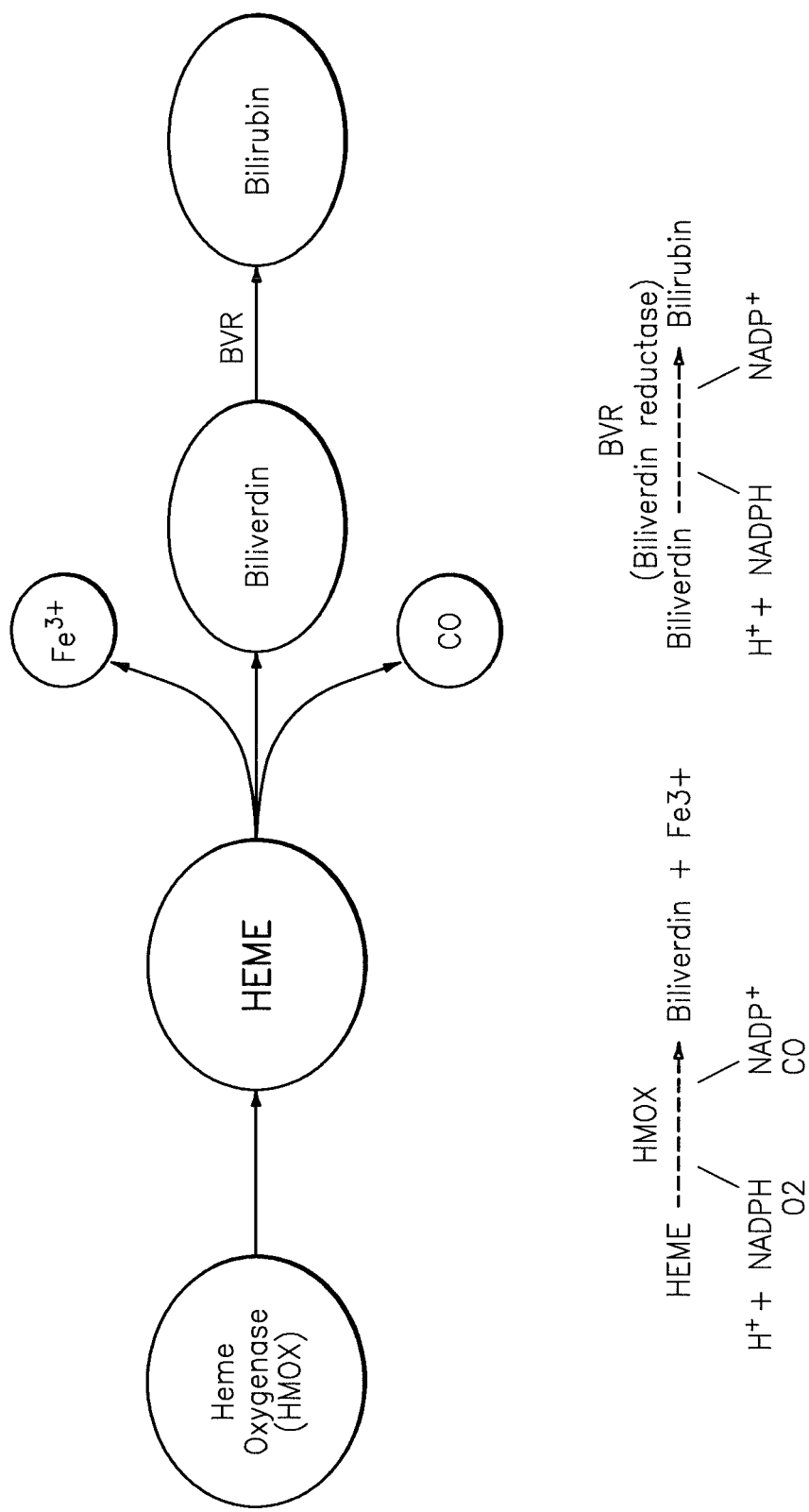
FIG. 2 is a diagrammatic illustration of the relationship of Heme Oxygenase and the constituents which come therefrom.
Figure 3:
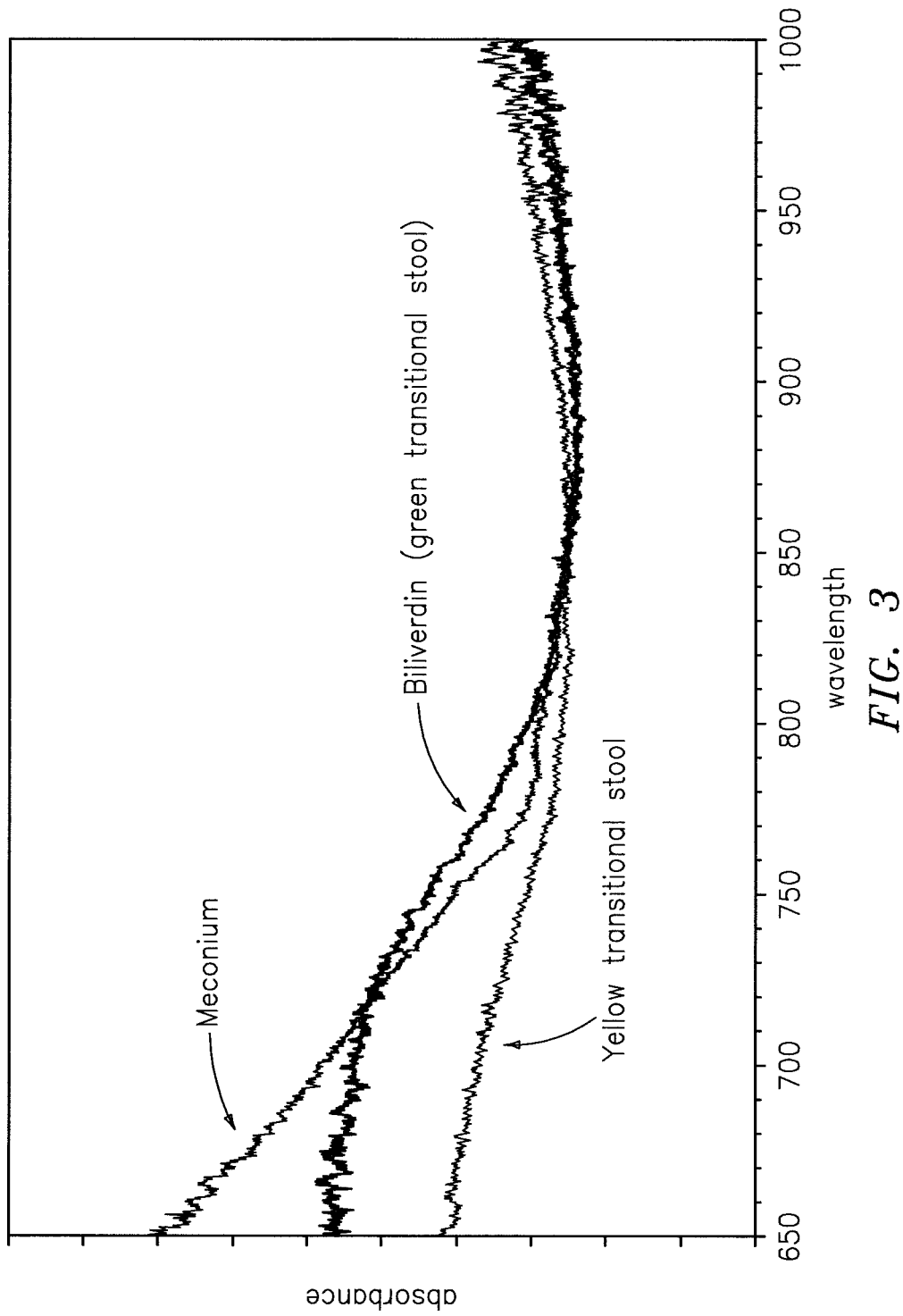
FIG. 3 is a graph depicting the relationship between absorbance and wavelength for meconium, biliverdin, and transitional stool.
Figure 3A:
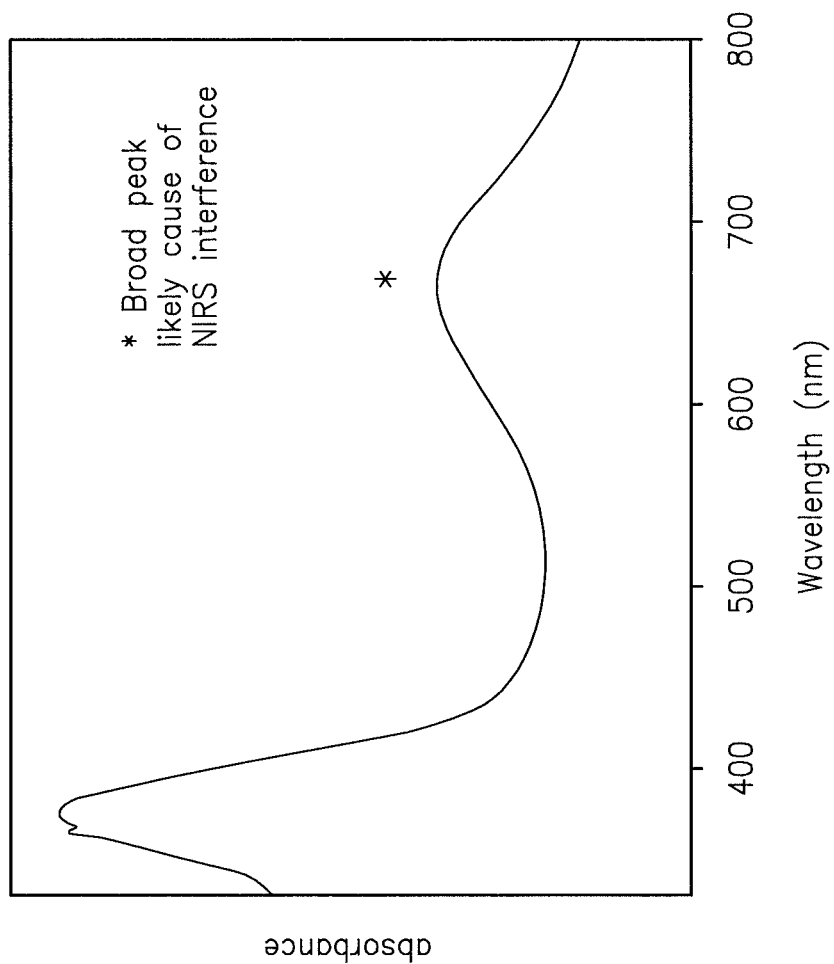
FIG. 3A is a graph depicting the relationship between the absorbance of isolated biliverdin, and wavelength
Figure 3B:
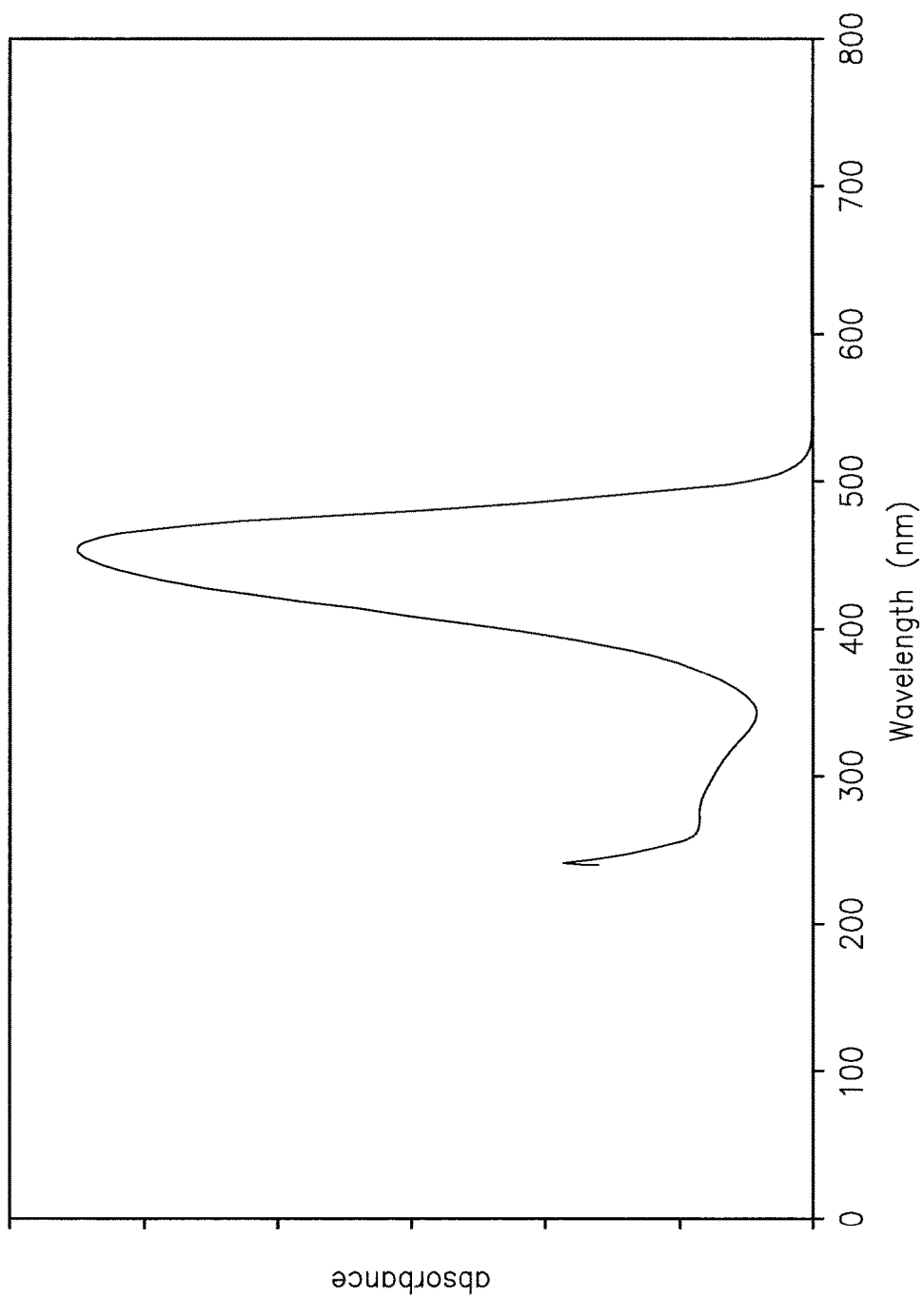
FIG. 3B is a graph depicting the relationship between the absorptance of isolated bilirubin, and wavelength.

For example, the empirical database may be organized in the form of a graph having Hb and HbO2 concentration corrective factors (e.g., $Z_{Hb}$ and $Z_{HbO2}$) plotted along the y-axis versus MECf index values plotted along the x-axis as shown in FIG. 8. In the example shown in FIG. 8, a statistically significant number of the data for each curve lies within the sloped portion (i.e., the portion that does not have a constant calibration constant value). At each end of the sloped portion, the curves are depicted as having constant calibration values for convenience sake.

The values for the subject-specific calibration coefficients $Z_{Hb}$ and $Z_{HbO2}$ are determined by drawing a line perpendicular to the MECf index value axis at the determined MECf index value. The corrective factor ($Z_{Hb}$) for deoxyhemoglobin is equal to the value on the calibration constant axis aligned with the intersection point between the perpendicular line and the "ZHb" curve, and the corrective factor ($Z_{HbO2}$) for oxyhemoglobin is equal to the value on the calibration constant axis aligned with the intersection point with the "ZHbO2" curve. Alternatively, the corrective factors $Z_{Hb}$ and $Z_{HbO2}$ as a function of MECf index may be determined using an empirical database in a form other than a graph. For example, a mathematical solution can be implemented rather than the above-described graph. The mathematical solution may use linear equations representing the "ZHb" and the "ZHbO2" curves. Alternatively, the corrective factors $Z_{Hb}$ and $Z_{HbO2}$ as a function of MECf index may use non-linear relationships to provide better accuracy in correcting for the concentrations of Hb and HbO2 in the presence of meconium.

Once the real-time Hb and HbO2 concentration corrective factors (e.g., $Z_{Hb}$ and $Z_{HbO2}$) are determined in the presence of meconium and/or nutritional fluids, they are utilized with a variation of Equation 13:

$$SnO_2 \% = \frac{(A_{HbO_2} - \Psi_{HbO_2} + Z_{HbO_2})}{(A_{HbO_2} - \Psi_{HbO_2} + Z_{HbO_2} + A_{Hb} - \Psi_{Hb} + Z_{Hb})} * 100\% \quad \text{(Eqn. 17)}$$

to determine the baby's lower GI blood oxygen saturation level.

The above-described process for determining the Hb and HbO2 concentration corrective factors can be performed at the same sampling frequency one or more times in the initial period of sensing the subject to calibrate the sensor to that particular subject, preferably right after the sensor is attached to the subject. The subject-specific calibration constants can then be used with an algorithm for measurement of a subject's blood oxygen saturation level using the same or different signal data. The subject-specific calibration constants can also be periodically updated in the manner described or constantly updated in real-time at the same sampling rate as $A_{Hb}$ and $A_{HbO2}$ are determined. The algorithm in which the subject-specific calibration constants are utilized may be the same algorithm as used to determine the constants, or a different algorithm for determining the tissue oxygen saturation level. For example, calibration constants can be used with the three 3-wavelength method disclosed above in Equations 2-14, and in U.S. Pat. No. 6,456,862, which is hereby incorporated by reference. Prior to the blood oxygen saturation level being calculated, the subject-specific calibration constants $Z_{Hb}$ and $Z_{HbO2}$ can be incorporated as corrective factors into the three wavelength algorithm (e.g., incorporated into Eqn. 13, as shown in Eqn. 17). As a result, a more accurate determination of the subject's tissue oxygen saturation level is possible. FIG. 7 illustrates the above described steps within a flow chart.

In alternative embodiments, the MECf index methodology disclosed above can be used within an algorithm in a subject-independent manner. This approach does not provide all of the advantages of the above described subject-dependent methodology and apparatus, but does provide improved accuracy by specifically accounting for subject meconium and/or nutritional fluids. For example, the MECf absorption coefficients ($\alpha_{MECf}$) can be determined as described above and utilized within Equation 15 or Equation 16 based on subject-independent empirical data such as that shown in FIG. 1. Regardless of the equation used, the determined values for deoxyhemoglobin (Hb) and oxyhemoglobin ($HbO_2$) can subsequently be used to determine the tissue oxygen saturation level. For example, the Hb and $HbO_2$ values can be utilized within Equations 11 through 13.

In an alternative embodiment, the present invention is operable to sense for the presence of meconium and/or nutritional fluids (or other wavelength dependent light absorbing material) in the lower GI tract using the calculated MECf data (or respective other data), and to display the MECf data as a waveform depicting the concentration of meconium and/or nutritional fluids in the lower GI tract over a period of time. MECf waveforms that are dynamic (e.g., change over a period of time) indicate that fecal matter has passed through the sensed section of the lower GI tract, which is an indication of a healthy bowel. A static (e.g., unchanged) MECf waveform could be indicative of a bowel blockage due to meconium or other causes. Mathematical analysis of the MECf waveforms may indicate intermediate stages of bowel health. For example, the MECf periodicity or frequency of meconium passage under the NIRS sensor may indicate the level of bowel health; e.g., a healthy subject is likely to have "n" number of bowel movements within a twenty-four hour period. Less or more than "n" number of movements may, therefore, be indicative of a potential problem.

In alternative embodiments, the MECf index could be determined without using equation 16. By using direct analysis of the absorption spectra of tissue, particularly the GI tract, the MECf index can be determined. To understand this concept, the absorption spectra of the tissue containing blood with different levels of hemoglobin oxygen saturation or SnO2 are shown in FIG. 9.

Figure 9:
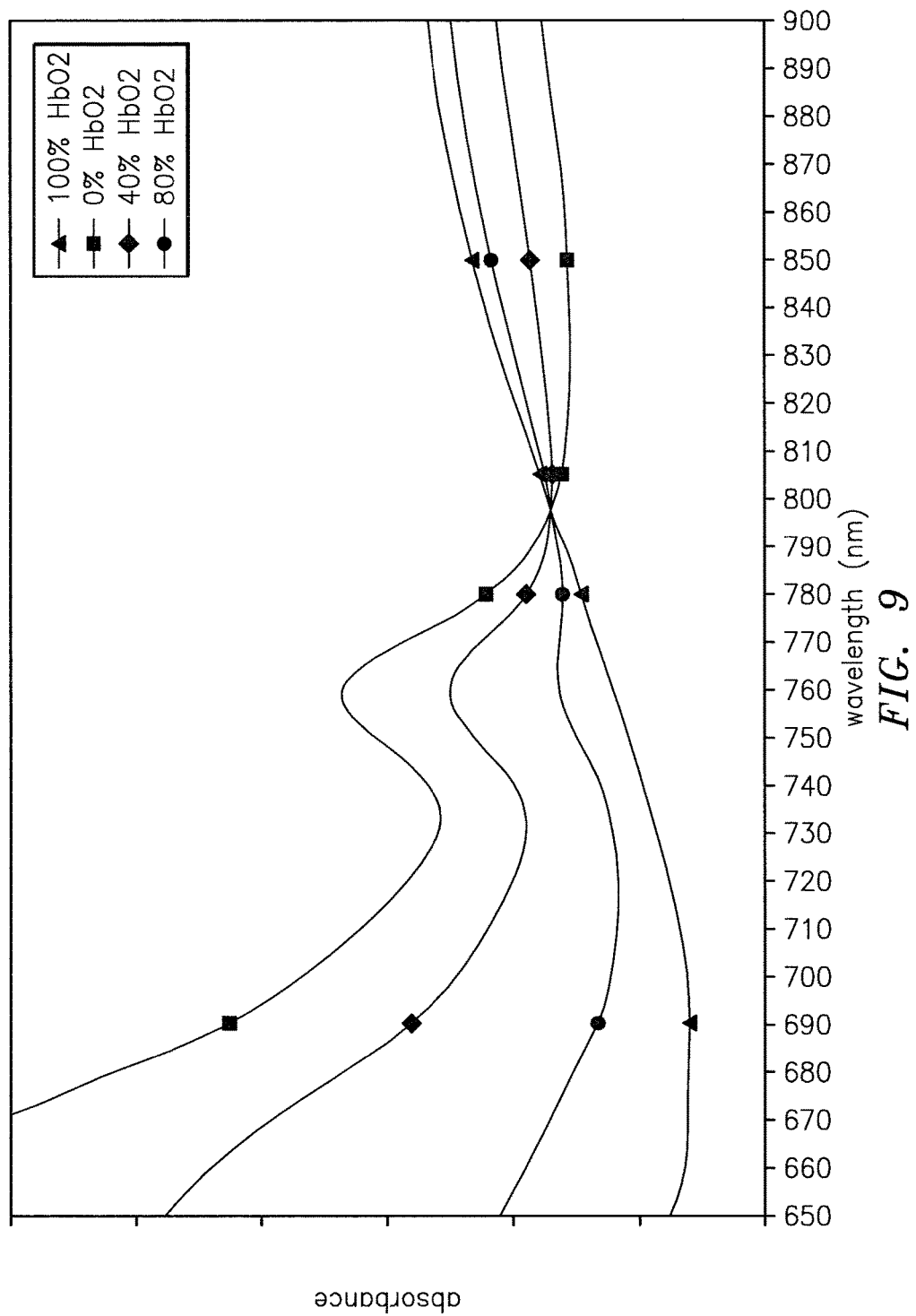
FIG. 9 is a graph diagrammatically illustrating absorbance of the tissue containing blood with different levels of hemoglobin oxygen saturation or SnO2.

The absorption spectra at different levels of hemoglobin oxygen saturation or SnO2 are derived from the Hb and HbO2 absorption spectra (FIG. 9). At a 100% oxygenated hemoglobin as depicted by the triangles (i.e. 100% HbO2 or 100% SnO2=HbO2/[HbO2+Hb]), the absorption spectra is that of HbO2. At a 0% oxygenated hemoglobin as depicted by the squares (i.e. 0% HbO2 or 0% SnO2=HbO2/[HbO2+Hb]), the absorption spectra is that of Hb or deoxy-hemoglobin. In between are different degrees of hemoglobin oxygen saturation or SnO2, which is determined by weighted absorption spectra of Hb and HbO2. For example, a hemoglobin O2 saturation or SnO2 of 80% would have an absorption spectrum that is weighted as 0.80×HbO2 absorption spectrum+0.20×Hb absorption spectrum. Understanding the characteristic of the hemoglobin oxygen saturation spectra from 0% to 100% is important especially in detecting other chromophores other than Hb and HbO2 in the same spectral wavelength range.

Figure 10:
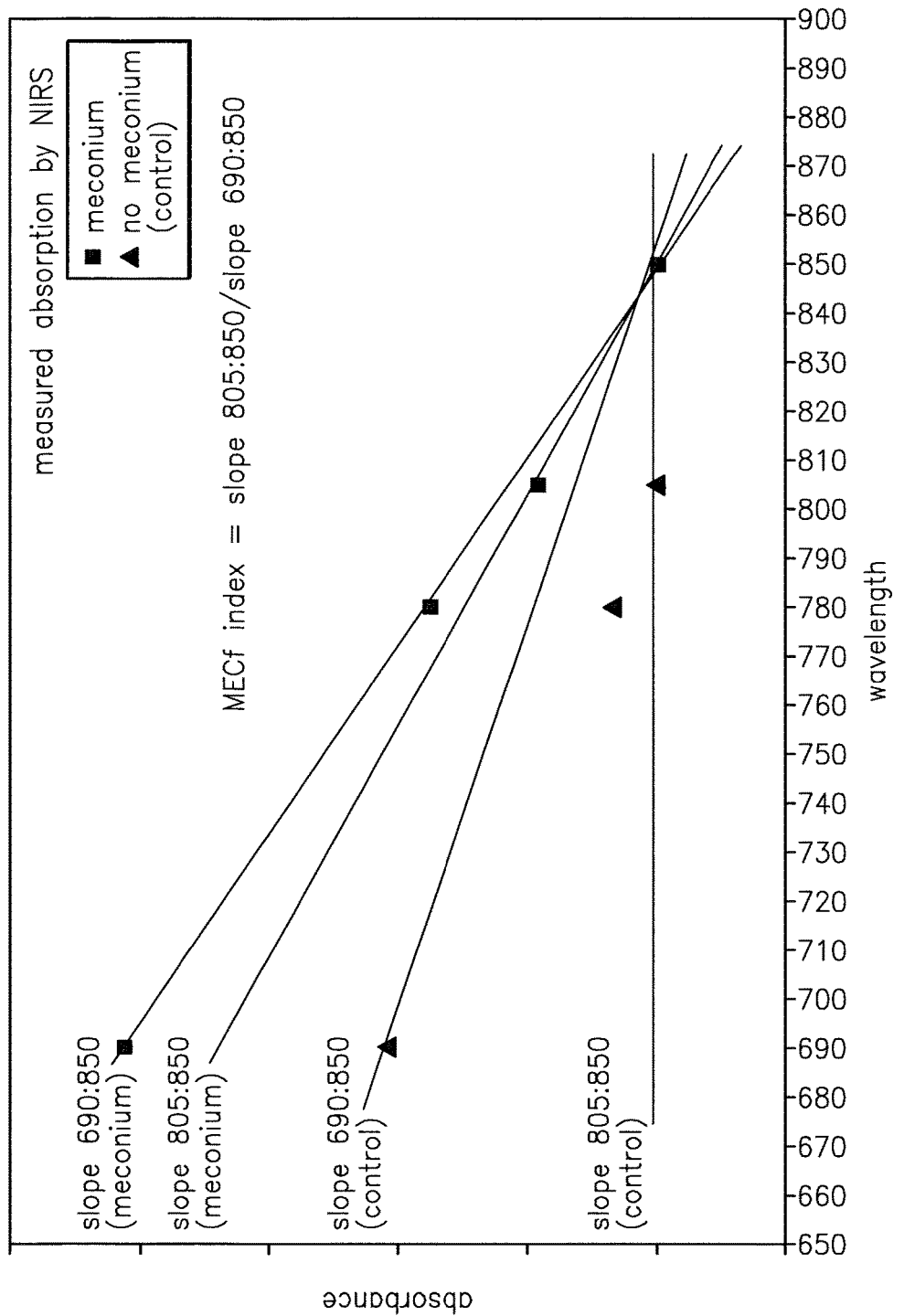
FIG. 10 is a graph diagrammatically illustrating using the absorbance slope method to detect chromophores other than Hb and HbO2.

Referring to FIG. 10, one such method to detect other chromophores in the 650-900 nm range is shown. In this example the NIRS absorption spectrum was measured by a NIRS sensor placed over the GI tract of a premature neonate. With no meconium present under the sensor, as represented by discrete measurements (triangles), hemoglobin oxygen saturation or SnO2 could be measured. When meconium was present under the NIRS sensor, the measured absorption spectrum changed as depicted by the squares. For this measured absorption spectrum, hemoglobin oxygen saturation or SnO2 could not be measured. If the four discrete absorption spectra data points represented by the squares were added to the hemoglobin O2 saturation spectra of FIG. 9, the data points would be outside the range of hemoglobin oxygen saturation or SnO2 of 0% to 100%. Thus, no SnO2 measurement could be made. Taking advantage of this information when meconium is present, several analytical methods could be employed. (Previously discussed Equation 16 employed a direct mathematical method to detect the presence of meconium.) One such method as shown in FIG. 10 involves measuring the slopes between the absorbance at two or more discrete wavelengths from actual subject data measured by the NIRS sensor over the GI tract.

In this method, discrete wavelengths 690, 805, and 850 nm are used to measure the absorbance of the GI tract. Then the slopes for the absorbance between 690 to 850 nm and 805 to 850 nm are determined by the equations, Slope690 and Slope805

$$\text{Slope690} = [-10001(850-690)] * \text{Log } 10[(I_{690}/Io_{690})/(I_{850}/Io_{850})] \quad \text{Eqn 18}$$

$$\text{Slope805} = [-1000/(850-805)] * \text{Log } 10[(I_{805}/Io_{805}/Io_{850})/(I_{850}/Io_{850})] \quad \text{Eqn 19}$$

Then the MECf index is determined by $$MECf \text{ index} = (\text{Slope805}/\text{Slope690}) * 100 \quad \text{Eqn 20}$$

This method works in detecting meconium because Slope805 is a high value compared to the slope of the absorbance between 805 and 850 nm for the full range of 0% to 100% hemoglobin oxygen saturation of FIG. 9. A high Slope805 value leads to a high MECf index value because Slope805 is in the numerator of the equation, especially as the value of Slope805 becomes similar to or greater than the Slope 690 value.

Figure 11:
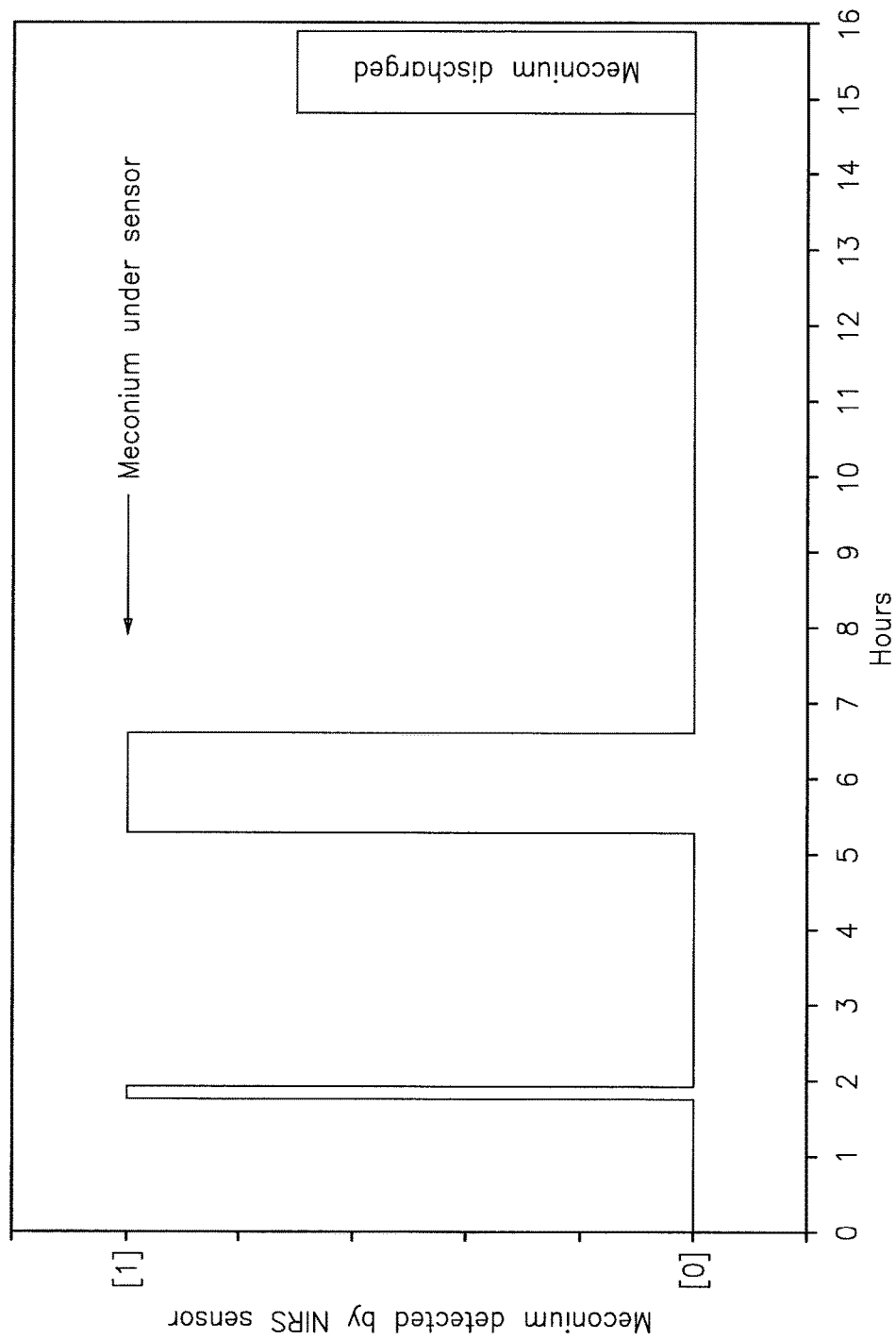
FIG. 11 is a graph diagrammatically illustrating meconium passing under the NIRS sensor prior to discharge.

When applied to physiological measurement, the MECf index should be greater than a predetermined value (i.e. MECf index>60 as an example) to indicate that a substantial quantity of meconium is present. If a GI tract motility indicator is desired as a binary waveform, then if MECf index is above the predetermined value, then the MECf index is "TRUE" or "1". Otherwise the MECf index is FALSE or "0". An example is shown in FIG. 11 from an actual recording. In this recording, meconium was present under the NIRS sensor several hours before a meconium stool is discharged.

Similar to that discussed previously, GI tract motility could then be determined by time domain or frequency analysis of the binary MECf index waveform. Also an index of GI tract motility could be determined by the percent of time that meconium was present under the sensor compared to the total monitoring time. If meconium is present at a high percentage of time under the sensor, impaired GI tract motility or a diseased state could be indicated.

The MECf index determined from this method can also be used to correct for meconium interference in calculating SnO2. If Equations 10-12 were used to determine $A_H$, and $A_{HbO2}$ to calculate SnO2, a corrective factor based on this method's MECf index can be employed much like FIG. 8:

$$Hb \text{ correction} = Z_{Hb} = \text{function}(MEFf \text{ index})$$

$$HbO2 \text{ correction} = Z_{HbO2} = \text{function}(MEFf \text{ index})$$

Then Equation 17 can be used to determine an accurate SnO2 in the presence of meconium or other chromophore matter in the GI tract. Note that this methodology is not limited to the GI tract or for meconium interference. Other organs or biological tissues that contain blood may also have interfering substances that need to be accounted for in accurate SnO2 measurement. For example, neonates passing transitional stools after the clearance of meconium typically show interference of the NIRS measurement for GI StO2, but to a lesser magnitude compared to meconium. This weaker transitional stool interference can also be adapted as a GI tract motility indicator and as a MECf index to compensate NIRS algorithms for accurate GI StO2 measurement. Also during the time of transitional stools, the neonate may be ingesting substances like iron rich milk that can cause the NIRS interfering effect. As the neonate matures and is on regular feeds, the interfering NIRS signal to determine the MECf index disappears. If an GI tract signal is desired to be monitored by NIRS, safe additives to the food ingested that are chromophores could be used as an NIRS contrasting agent to monitor GI tract motility under an NIRS sensor.

Figure 12:
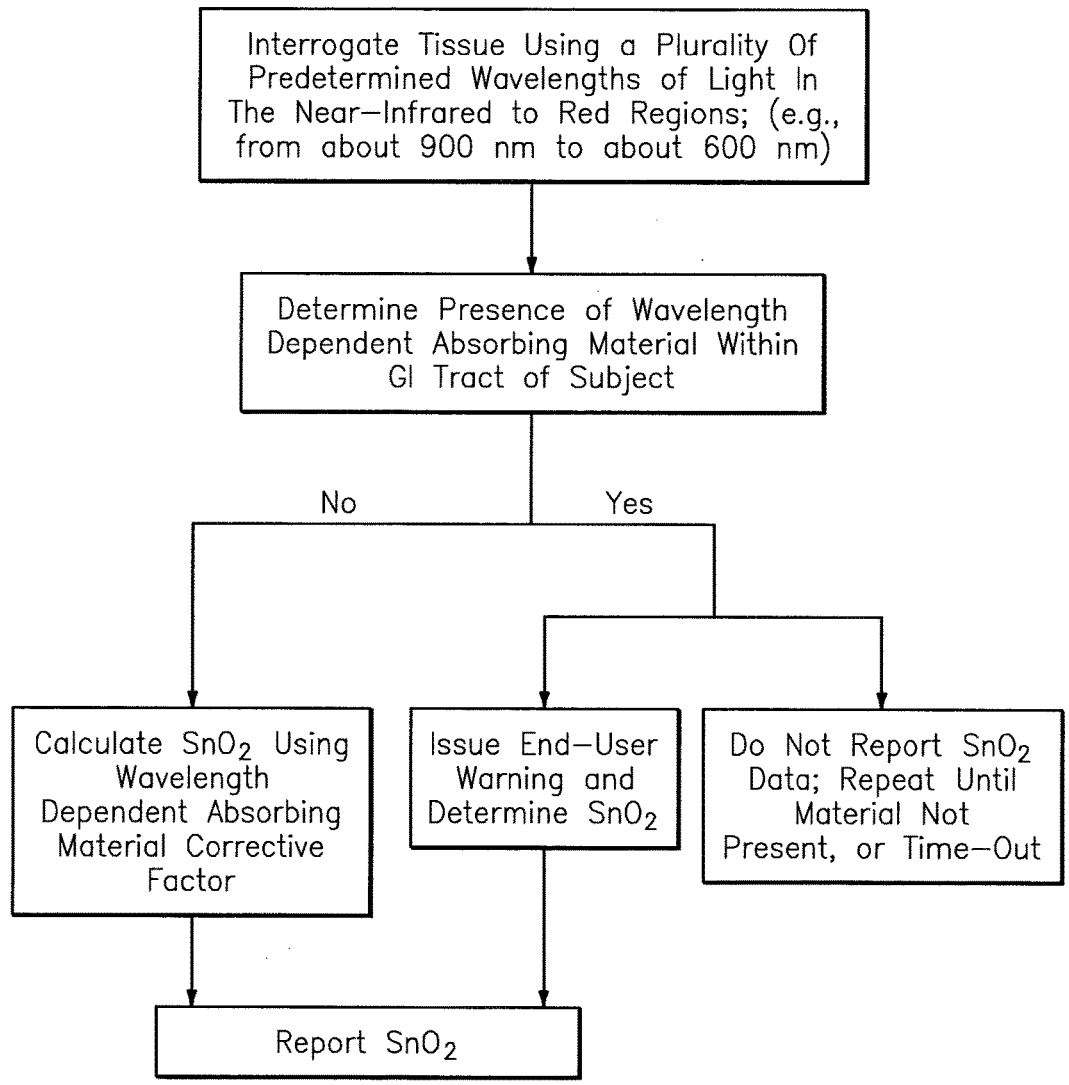
FIG. 12 is a flow chart illustrating steps according to another aspect of the present invention.

In another alternative embodiment, the present invention is operable to sense for the presence of meconium and/or nutritional fluids (or other wavelength dependent light absorbing material) in the lower GI tract and use the sensed signal data to alert the user that meconium and/or nutritional fluids are present. The flow chart shown in FIG. 12 illustrates the algorithm of this embodiment. In those instances when meconium and/or nutritional fluids are present, NIRS-type sensors that do not account for meconium and/or nutritional fluids will likely indicate an erroneous oxygen saturation value. Using the present invention, however, the presence of meconium, including stool components such as biliverdin, and/or nutritional fluids can be determined and thereby accounted for; i.e., either prevent a determination the oxygen saturation value until the level of meconium, including stool components such as biliverdin, and/or nutritional fluids drops below a predetermined value where it will not materially affect the oxygenation determination, or issue a warning to the end-user that the presence of meconium could adversely affect the accuracy of the oxygenation determination, or use a corrective factor that takes into consideration the amount of meconium, including stool components such as biliverdin, and/or nutritional fluids present within the subject's lower GI tract when making the determination.

Although the present method and apparatus are described above in exemplary terms of sensing blood oxygenation within the lower GI tract of an infant, the present method and apparatus are not limited to such applications and can be used to determine tissue blood oxygenation saturation within the lower GI tract of subjects older than an infant. For example, bile and iron-rich fluids (and perhaps other interfering chromophores) may be present within the feces of children and adults. As a result, the present invention method and apparatus can be used to determine the tissue blood oxygenation saturation percentage in the lower GI tract of such subjects.

To illustrate the utility of the present invention, a pair of studies are briefly described below, each illustrating an embodiment of the present invention. These studies are provided as illustrative examples only, and the present invention is not limited to these embodiments.

Meconium Interferes with NIRS Measurements of the GI Tract in Premature Neonates:

In a first study, NIRS GI StO2 measurements and Doppler measurements of superior mesenteric artery flow in preterm neonates were determined and compared. During the study, we found that the GI StO2 measurements varied widely from patient to patient, leading us to investigate possible causes.

A meconium sample was obtained from a preterm infant and a portion was analyzed by a bench top spectrometer (EPP2000, Stellar Net, Inc., Tampa, Fla. USA). The remaining meconium sample was placed in an optically clear plastic bag and pressed out to form a translucent film. Two commercially available NIRS monitors, FORE-SIGHT (CASMED, Branford, Conn. USA) and one from a different manufacturer were tested with NIRS sensors placed on an adult forearm. The meconium film was then inserted between the sensors and the forearm to detect possible changes in NIRS values.

Figure 13:
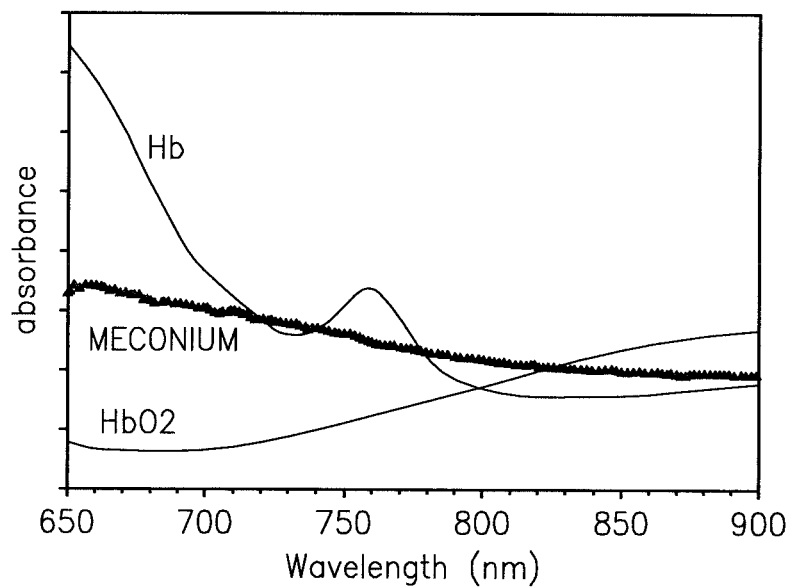
FIG. 13 is a graph of absorption versus wavelength showing the absorption spectra of meconium versus Hb and HbO2.

The light absorption spectrum of the meconium was plotted along with oxy-hemoglobin (HbO2) and deoxy-hemoglobin (Hb) for NIRS wavelengths 650-900 nm (see FIG. 13 below). The meconium absorption spectra decreases with increasing wavelength in the NIRS range. When testing the translucent meconium film with both NIRS monitors, the measured StO2 dropped significantly to either very low or no values, as a function of meconium film thickness.

The tests performed using meconium samples from a preterm infant in both a spectrometer and the available NIRS monitors demonstrated that meconium can interfere with NIRS StO2 measurement, resulting in falsely low values. Measurement of Mesenteric Tissue Oxygen Saturation (GI StO2%) on Premature Infants:

In a second study, NIRS monitoring of mesenteric tissue was performed on preterm infants undergoing enteral feeds to determine if evidence of bowel ischemia is present. Interpretation of such data may be limited, however, with interference secondary to the presence of meconium in the intestine. With parental agreement, we used a 4-wavelength cerebral & tissue oximeter (FORE-SIGHT®, CAS Medical Systems, Branford, Conn. USA) to monitor premature neonates for 72 hours. The oximeter sensors were placed in the right lower quadrant of the abdomen and the forehead, with continuous data collection every 2 seconds for 72 hours to measure GI and brain StO2. Simultaneously, continuous peripheral pulse oximetry (SpO2) was measured using a Masimo pulse oximeter, (Irvine, Calif.). In addition, feeding regimen and stooling patterns were recorded, as well as clinical outcomes including feeding intolerance and development of NEC. Raw data from FORE-SIGHT was recorded to understand the effects of stool related interference due to the passage of meconium and transitional stools on GI StO2 measurement. The percent time of high stool interference under the NIRS sensor was recorded as a possible bowel motility indicator and correlated with outcome.

Figure 15:
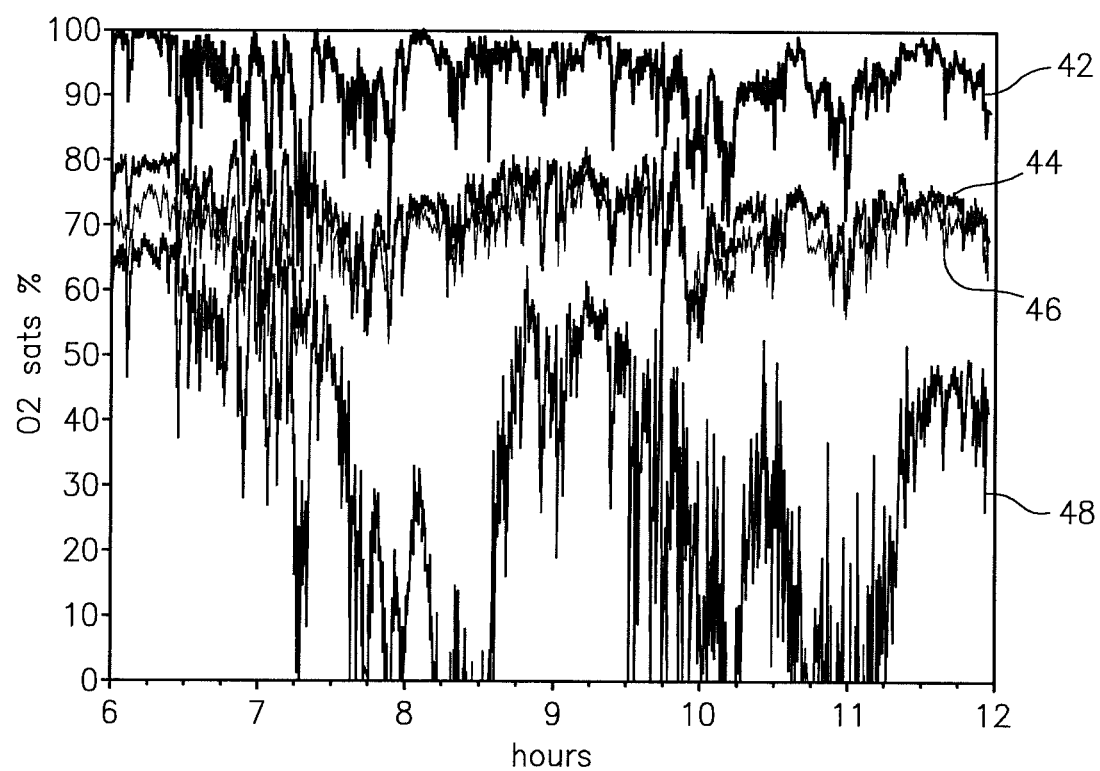
FIG. 15 is a graph of oxygen saturation percentage as a function of time for a gastrointestinal tract.
Figure 16:
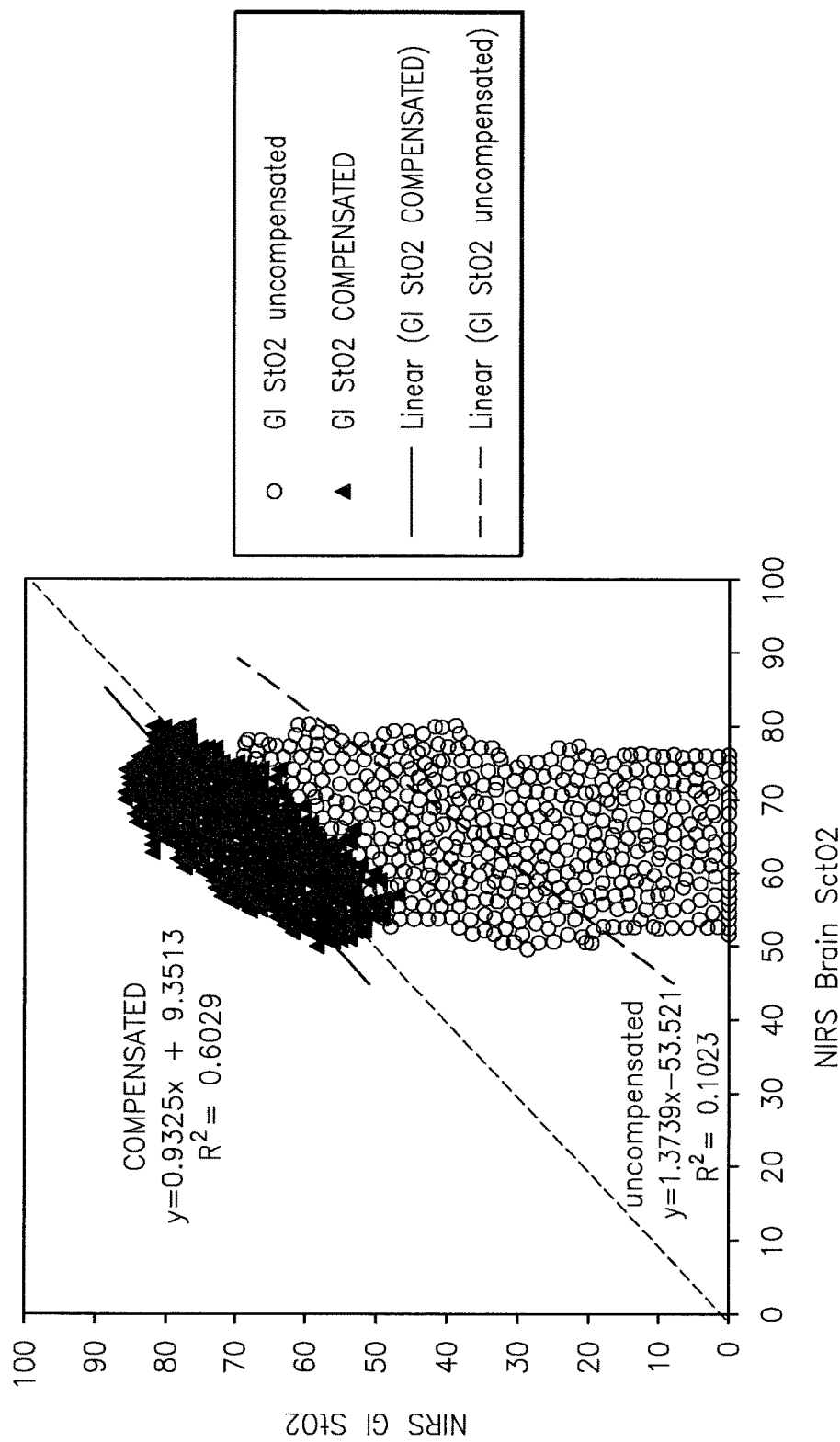
FIG. 16 is a graph of gastrointestinal tract oxygen saturation versus cerebral oxygen tissue saturation.

Fifteen preterm neonates with gestational ages of 29-34 weeks, weighing 980-1800 grams were studied. NIRS stool interference level and percentage of high stool interference detected by NIRS to overall monitor time was determined for all subjects as listed in Table 1, which is shown in FIG. 14. The detected stool interference level tended to be very variable, likely due to the passage of stools under the NIRS sensor. Impaired bowel motility may cause the NIRS detected stool interference to remain at a high level for a large percentage of the monitoring time. Coincidentally, two subjects developed NEC with prolonged high NIRS stool interference. High stool interference usually but not always occurred for subjects passing meconium. Moderate and High stool interference resulted in erroneously computed very low GI StO2 using traditional NIRS methods as shown by the uncompensated GI StO2 48 in FIGS. 15 and 16. FIGS. 15 and 16 also show the results of a prototype NIRS algorithm that uses the NIRS measured stool interference to compensate for errors in calculating GI StO2 as displayed by the compensated GI StO2 44. The compensated GI StO2 44 generally showed a high correlation to brain StO2 46 and pulse oximetry SpO2 42 for healthy bowel subjects.

As our results demonstrate, the presence of meconium and transitional stools causes variable interference in the measurement of mesenteric tissue oxygenation, which when compensated for in the NIRS algorithm, permits a significant increase in the accuracy of the GI tissue oxygen saturation. The present invention NIRS system utilizes at least 3 wavelengths, as the chromophore(s) contained in newborn stools become the third unknown to be calculated, along with oxy- and deoxy-hemoglobin, which is used to calculate StO2%.

Since many changes and variations of the disclosed embodiment of the invention may be made without departing from the inventive concept, it is not intended to limit the invention otherwise than as required by the appended claims.

What is claimed is:

1. A method for non-invasively determining a blood oxygen saturation level within a subject's lower gastrointestinal (GI) tissue, which tissue defines a lower GI tract of the subject, comprising:
   non-invasively sensing the subject's lower GI tissue using a spectrophotometric sensor having at least one light source and at least one light detector, which sensing includes transmitting light from the light source into the subject's lower GI tissue and GI tract at a plurality of wavelengths in a range of about 600 nm to about 900 nm at an initial intensity, and sensing the transmitted light after passage of the transmitted light through the subject's lower GI tissue and lower GI tract using the at least one light detector, and producing signal data representative of a detected intensity of the sensed light;
   using at least one processor to determine:
      an attenuation between the initial intensity and the detected intensity of one or more wavelengths of the plurality of wavelengths of light;
      an index value that accounts for the presence of one or more wavelength dependent light absorbing materials disposed within the subject's lower GI tract, which absorbing materials are not present in the subject's blood, based on the determined attenuation;
      at least one corrective factor value based on the index value when the index value is above a predetermined value; and
      the blood oxygen saturation level within the subject's lower GI tissue, which blood oxygen saturation level determination includes using the at least one corrective factor value when the at least one corrective factor value is determined.

2. The method of claim 1, wherein the one or more wavelength dependent light absorbing material includes at least one of meconium, transitional stool, biliverdin, or nutritional fluid.

3. The method of claim 2, wherein the at least one corrective factor value includes a deoxyhemoglobin (Hb) corrective factor value and an oxyhemoglobin (HbO2) corrective factor value.

4. The method of claim 2, wherein the at least one corrective factor value varies as a function of the determined attenuation of the one or more wavelengths of the plurality of wavelengths of light, which one or more wavelengths includes at least one wavelength in a red spectrum of visible light.

5. The method of claim 4, wherein the red spectrum of light is between about 600 nm to about 780 nm.

6. The method of claim 5, wherein the at least one wavelength in the red spectrum of light is about 690 nm.

7. A near-infrared spectroscopy apparatus for non-invasively determining a blood oxygen saturation level within a subject's lower gastrointestinal (GI) tissue, which tissue defines a lower GI tract of the subject, comprising:
   a non-invasive spectrophotometric sensor having at least one light source that selectively transmits light at a plurality of wavelengths in a range of about 600 nm to about 900 nm at an initial intensity value, and at least one light detector configured to sense the light transmitted from the at least one light source after such light has passed through the subject's lower GI tissue and lower GI tract, which the at least one light detector produces signal data representative of a detected intensity of the sensed light; and a processor programmed within a non-transitory memory to control the sensor and to receive the signal data, and to determine:
- an attenuation between the initial intensity and the detected intensity of one or more wavelengths of the plurality of wavelengths of light;
- an index value that accounts for the presence of one or more wavelength dependent light absorbing materials disposed within the subject's lower GI tract, which absorbing materials are not present in the subject's blood, based on the determined attenuation;
- at least one corrective factor value based on the index value when the index value is above a predetermined value; and
- the blood oxygen saturation level within the subject's lower GI tissue, which blood oxygen saturation level determination includes using the at least one corrective factor value when the at least one corrective factor value is determined.

8. The apparatus of claim 7, wherein the one or more wavelength dependent absorbing material includes at least one of meconium, transitional stool, biliverdin, or nutritional fluid.

9. The apparatus of claim 8, wherein the plurality of wavelengths includes one or more wavelengths having an absorbance value magnitude for the one or more wavelength dependent light absorbing materials that is different from an absorbance value magnitude for oxyhemoglobin ($HbO_2$) or an absorbance value magnitude for deoxyhemoglobin (Rb) at the same one or more wavelengths.

10. The apparatus of claim 8, wherein the at least one corrective factor value includes a deoxyhemoglobin (Hb) corrective factor value and an oxyhemoglobin ($HbO_2$) corrective factor value.

11. The apparatus of claim 8, wherein the at least one corrective factor value varies as a function of the determined attenuation of the one or more wavelengths of the plurality of wavelengths of light, which one or more wavelengths includes at least one wavelength in a red spectrum of visible light.

12. The apparatus of claim 11, wherein the red spectrum of light is between about 600 nm to about 780 nm.

13. The apparatus of claim 11, wherein the at least one wavelength in the red spectrum of light is about 690 nm.

* * * * *